US007910613B2

United States Patent

(12) United States Patent
Larsen et al.

(10) Patent No.: US 7,910,613 B2
(45) Date of Patent: Mar. 22, 2011

(54) 2-ACYLAMINOTHIAZOLE DERIVATIVES

(75) Inventors: Mogens Larsen, Smorum (DK); Annette Graven Sams, Vaerlose (DK); Gitte Mikkelsen, Ballerup (DK); Benny Bang-Andersen, Copenhagen S. (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 1040 days.

(21) Appl. No.: 11/663,054

(22) PCT Filed: Sep. 20, 2005

(86) PCT No.: PCT/DK2005/000591

§ 371 (c)(1), (2), (4) Date: Mar. 16, 2007

(87) PCT Pub. No.: WO2006/032273

PCT Pub. Date: Mar. 30, 2006

(65) Prior Publication Data

US 2009/0137642 A1 May 28, 2009

Related U.S. Application Data

(60) Provisional application No. 60/612,236, filed on Sep. 22, 2004.

(30) Foreign Application Priority Data

Sep. 22, 2004 (DK) ................................ 2004 01441

(51) Int. Cl.

*A61K 31/245* (2006.01)
*A61K 31/426* (2006.01)
*C07D 277/20* (2006.01)
*C07D 271/06* (2006.01)

(52) U.S. Cl. ......... 514/364; 548/195; 548/131; 514/131

(58) Field of Classification Search .................. 514/364, 514/371; 548/131, 195

See application file for complete search history.

(56) References Cited

U.S. PATENT DOCUMENTS

| | | | |
|---|---|---|---|
| 5,344,736 | A | 9/1994 | Komiyama et al. |
| 6,140,330 | A | 10/2000 | Mori et al. |
| 6,727,269 | B1 | 4/2004 | Moinet et al. |
| 2004/0053982 | A1 | 3/2004 | Press et al. |
| 2004/0138235 | A1 | 7/2004 | Grzelak et al. |
| 2004/0235888 | A1 | 11/2004 | Yamamori et al. |
| 2006/0154974 | A1 | 7/2006 | Sams et al. |
| 2006/0264485 | A1 | 11/2006 | Sams et al. |
| 2007/0105919 | A1 | 5/2007 | Nakajima et al. |

FOREIGN PATENT DOCUMENTS

| | | | |
|---|---|---|---|
| DE | 855 120 | C | 1/1953 |
| EP | 0 407 200 | A1 | 1/1991 |
| EP | 0 870 765 | A1 | 10/1998 |
| EP | 0 934 938 | A1 | 8/1999 |
| EP | 1 176 139 | A1 | 1/2002 |
| EP | 1 295 872 | A1 | 3/2003 |
| EP | 1 354 880 | A1 | 10/2003 |
| WO | WO 99/64418 | A1 | 12/1999 |
| WO | WO 00/26202 | A1 | 5/2000 |
| WO | WO 00/62778 | A1 | 10/2000 |
| WO | WO 02/055083 | A1 | 7/2002 |
| WO | WO 03/045386 | A1 | 6/2003 |
| WO | WO 03/053946 | A1 | 7/2003 |
| WO | WO 03/057689 | | 7/2003 |
| WO | WO 2004/085388 | A2 | 10/2004 |
| WO | WO 2005/037779 | A2 | 4/2005 |
| WO | WO 2005/039572 | A1 | 5/2005 |
| WO | WO 2005/094376 | A2 | 10/2005 |
| WO | WO 2006/028958 | A2 | 3/2006 |
| WO | WO 2006/051704 | A1 | 5/2006 |
| WO | WO 2007/015528 | A1 | 2/2007 |
| WO | WO 2007/022415 | A2 | 2/2007 |

OTHER PUBLICATIONS

Blum, D., et al. A Dual Role of Adenosine A 2A Receptors in 3-Nitropropionic Acid-Induced Striatal Lesions: Implications for the Neuroprotective Potential of A 2A Antagonists. J. Neurosci. Jun. 15, 2003. 23(12):5361-5369.
CAS Registry No. 768290-60-4; Oct. 24, 2004; Chemical Library Supplier Vitas-M.
CAS Registry No. 763063-10-1; Oct. 15, 2004.
CAS Registry No. 760925-04-0; Oct. 11, 2004.
CAS Registry No. 757167-34-3; Oct. 6, 2004.
CAS Registry No. 734518-98-0; Aug. 27, 2004.
CAS Registry No. 728930-56-1; Aug. 19, 2004; Chemical Library Supplier Vitas-M.
CAS Registry No. 702647-52-7; Jul. 2, 2004; Chemical Library Supplier ChemBridge Corporation.
CAS Registry No. 693819-92-0; Jun. 16, 2004; Chemical Library Supplier ChemBridge Corporation.
CAS Registry No. 693814-29-8; Jun. 16, 2004; Chemical Library Supplier ChemBridge Corporation.
CAS Registry No. 693808-23-0; Jun. 16, 2004; Chemical Library Supplier ChemBridge Corporation.
CAS Registry No. 693805-33-3; Jun. 16, 2004; Chemical Library Supplier ChemBridge Corporation.
CAS Registry No. 693795-29-8; Jun. 16, 2004; Chemical Library Supplier ChemBridge Corporation.
CAS Registry No. 693265-95-1; Jun. 15, 2004; Chemical Library Supplier ChemBridge Corporation.
CAS Registry No. 693265-12-2; Jun. 15, 2004; Chemical Library Supplier ChemBridge Corporation. CAS Registry No. 686739-77-5; May 28, 2004; Chemical Library Supplier ChemDiv, Inc.
CAS Registry No. 667410-90-4; Mar. 25, 2004; Chemical Library Supplier Scientific Exchange, Inc.
CAS Registry No. 667410-45-9; Mar. 25, 2004; Chemical Library Supplier Scientific Exchange, Inc.
CAS Registry No. 667403-59-0; Mar. 25, 2004; Chemical Library Supplier Scientific Exchange, Inc.
CAS Registry No. 663185-58-8; Mar. 15, 2004; Chemical Library Supplier ChemBridge Corporation.
CAS Registry No. 663185-33-9; Mar. 15, 2004; Chemical Library Supplier Vitas-M.
CAS Registry No. 547758-27-0; Jul. 14, 2003; Chemical Library Supplier Ambinter.

(Continued)

*Primary Examiner* — Jennifer M Kim

(57) ABSTRACT

The Invention relates to compounds of the formula I, wherein the variables are as defined in the claims, for use as a medicament. The compounds are $A_{2A}$-receptor legends and are useful in the treatment of neurological and psychiatric disorders where an $A_{2A}$-receptor is implicated.

10 Claims, No Drawings

OTHER PUBLICATIONS

CAS Registry No. 547758-03-2; Jul. 14, 2003; Chemical Library Supplier Ambinter.
CAS Registry No. 546092-64-2; Jul. 11, 2003; Chemical Library Supplier Ambinter.
CAS Registry No. 545428-66-8; Jul. 10, 2003; Chemical Library Supplier Ambinter.
CAS Registry No. 502170-70-9; Apr. 8, 2003.
CAS Registry No. 500538-95-4; Mar. 25, 2003.
CAS Registry No. 500350-68-5; Mar. 24, 2003; Chemical Library Supplier Ambinter.
CAS Registry No. 500263-48-9; Mar. 23, 2003; Chemical Library Supplier Interchim.
CAS Registry No. 500262-43-1; Mar. 23, 2003; Chemical Library Supplier Interchim.
CAS Registry No. 443748-99-0; Aug. 13, 2002; Chemical Library Supplier Ambinter.
CAS Registry No. 428840-18-0; Jun. 12, 2002; Chemical Library Supplier ChemBridge Corporation.
CAS Registry No. 428503-55-3; Jun. 11, 2002; Chemical Library Supplier ChemBridge Corporation.
CAS Registry No. 405902-02-5; Apr. 18, 2002; Chemical Library Supplier Ambinter.
CAS Registry No. 404898-48-2; Apr. 10, 2002; Chemical Library Supplier Ambinter.
CAS Registry No. 404845-99-4; Apr. 9, 2002; Chemical Library Supplier ChemBridge Corporation.
CAS Registry No. 404832-67-3; Apr. 9, 2002; Chemical Library Supplier ChemBridge Corporation.
CAS Registry No. 404831-52-3; Apr. 9, 2002; Chemical Library Supplier Ambinter.
CAS Registry No. 404593-33-5; Apr. 8, 2002; Chemical Library Supplier Ambinter.
CAS Registry No. 404586-56-7; Apr. 8, 2002; Chemical Library Supplier Scientific Exchange, Inc.
CAS Registry No. 404585-17-7; Apr. 8, 2002; Chemical Library Supplier ChemBridge Corporation.
CAS Registry No. 404584-87-8; Apr. 8, 2002; Chemical Library Supplier Ambinter.
CAS Registry No. 404583-73-9; Apr. 8, 2002; Chemical Library Supplier Interchim.
CAS Registry No. 404378-49-0; Apr. 5, 2002; Chemical Library Supplier Ambinter.
CAS Registry No. 404370-61-2; Apr. 5, 2002; Chemical Library Supplier Ambinter.
CAS Registry No. 404362-66-9; Apr. 5, 2002; Chemical Library Supplier Interchim.
CAS Registry No. 402598-30-5; Mar. 22, 2002; Chemical Library Supplier Scientific Exchange, Inc.
CAS Registry No. 402597-41-5; Mar. 22, 2002; Chemical Library Supplier Ambinter.
CAS Registry No. 402583-28-2; Mar. 22, 2002; Chemical Library Supplier Ambinter.
CAS Registry No. 385388-07-8; Jan. 22, 2002; Chemical Library Supplier Interbioscreen, Ltd.
CAS Registry No. 384369-81-7; Jan. 19, 2002; Chemical Library Supplier Interbioscreen, Ltd.
CAS Registry No. 381707-47-7; Jan. 10, 2002; Chemical Library Supplier Interbioscreen, Ltd.
CAS Registry No. 381705-82-4; Jan. 10, 2002; Chemical Library Supplier Interbioscreen, Ltd.
CAS Registry No. 380578-78-9; Jan. 7, 2002; Chemical Library Supplier Interbioscreen, Ltd.
CAS Registry No. 380563-05-3; Jan. 7, 2002; Chemical Library Supplier Interbioscreen, Ltd.
CAS Registry No. 372953-39-4; Dec. 3, 2001.
CAS Registry No. 371117-55-4; Nov. 20, 2001; Chemical Library Supplier Interbioscreen, Ltd.
CAS Registry No. 364748-43-6; Oct. 26, 2001; Chemical Library Supplier Ambinter.
CAS Registry No. 364748-39-0; Oct. 26, 2001; Chemical Library Supplier Ambinter.
CAS Registry No. 364620-93-9; Oct. 25, 2001; Chemical Library Supplier ChemBridge Corporation.
CAS Registry No. 364619-30-7; Oct. 25, 2001; Chemical Library Supplier Scientific Exchange, Inc.
CAS Registry No. 364599-62-2; Oct. 25, 2001; Chemical Library Supplier Ambinter.
CAS Registry No. 355403-34-8; Sep. 10, 2001; Chemical Library Supplier ChemStar, Ltd.
CAS Registry No. 354121-19-0; Aug. 31, 2001; Chemical Library Supplier Scientific Exchange, Inc.
CAS Registry No. 351988-92-6; Aug. 20, 2001; Chemical Library Supplier Scientific Exchange, Inc.
CAS Registry No. 351498-95-8; Aug. 16, 2001; Chemical Library Supplier Scientific Exchange, Inc.
CAS Registry No. 349623-95-6; Aug. 1, 2001; Chemical Library Supplier Microchemistry Ltd.
CAS Registry No. 339207-36-2; Jun. 1, 2001; Chemical Library Supplier Zelinsky Institute of Organic Chemistry.
CAS Registry No. 333438-99-6; Apr. 30, 2001; Chemical Library Supplier AsInEx.
CAS Registry No. 333435-53-3; Apr. 30, 2001; Chemical Library Supplier AsInEx.
CAS Registry No. 333343-28-5; Apr. 27, 2001; Chemical Library Supplier Scientific Exchange, Inc.
CAS Registry No. 333343-27-4; Apr. 27, 2001; Chemical Library Supplier Scientific Exchange, Inc.
CAS Registry No. 332033-29-1; Apr. 23, 2001; Chemical Library Supplier AsInEx.
CAS Registry No. 330831-74-8; Apr. 11, 2001; Chemical Library Supplier Scientific Exchange, Inc.
CAS Registry No. 330828-15-4; Apr. 11, 2001; Chemical Library Supplier Ambinter.
CAS Registry No. 330634-85-0; Apr. 10, 2001; Chemical Library Supplier ChemDiv, Inc.
CAS Registry No. 312595-57-6; Jan. 3, 2001; Chemical Library Supplier ChemDiv, Inc.
CAS Registry No. 312595-53-2; Jan. 3, 2001; Chemical Library Supplier AsInEx.
CAS Registry No. 312533-59-8; Jan. 2, 2001; Chemical Library Supplier Scientific Exchange, Inc.
CAS Registry No. 312518-75-5; Jan. 2, 2001; Chemical Library Supplier Chemical Block, Ltd.
CAS Registry No. 311314-47-3; Dec. 27, 2000; Chemical Library Supplier ChemDiv, Inc.
CAS Registry No. 309283-62-3; Dec. 18, 2000; Chemical Library Supplier ChemDiv, Inc.
CAS Registry No. 305358-93-4; Nov. 30, 2000; Chemical Library Supplier Scientific Exchange, Inc.
CAS Registry No. 305358-92-3; Nov. 30, 2000; Chemical Library Supplier Scientific Exchange, Inc.
CAS Registry No. 305358-91-2; Nov. 30, 2000; Chemical Library Supplier Scientific Exchange, Inc.
CAS Registry No. 305358-90-1; Nov. 30, 2000; Chemical Library Supplier Scientific Exchange, Inc.
CAS Registry No. 305358-09-2; Nov. 30, 2000; Chemical Library Supplier Scientific Exchange, Inc.
CAS Registry No. 304507-98-0; Nov. 27, 2000; Chemical Library Supplier AsInEx.
CAS Registry No. 302958-93-6; Nov. 15, 2000.
CAS Registry No. 302958-46-9; Nov. 15, 2000.
CAS Registry No. 302927-86-2; Nov. 15, 2000; Chemical Library Supplier AsInEx.
CAS Registry No. 294891-94-4; Oct. 12, 2000; Chemical Library Supplier AsInEx.
CAS Registry No. 294891-92-2; Oct. 12, 2000; Chemical Library Supplier AsInEx.
CAS Registry No. 294890-49-6; Oct. 12, 2000; Chemical Library Supplier ChemDiv, Inc.
CAS Registry No. 292072-63-0; Oct. 2, 2000.
CAS Registry No. 292071-57-9; Oct. 2, 2000; Chemical Library Supplier Scientific Exchange, Inc.
CAS Registry No. 292070-16-7; Oct. 2, 2000.
CAS Registry No. 271773-11-6; Jun. 21, 2000.
CAS Registry No. 267657-40-9; Jun. 1, 2000.

CAS Registry No. 267657-39-6; Jun. 1, 2000.
CAS Registry No. 267657-38-5; Jun. 1, 2000.
CAS Registry No. 267656-13-3; Jun. 1, 2000.
CAS Registry No. 267656-12-2; Jun. 1, 2000.
CAS Registry No. 267656-11-1; Jun. 1, 2000.
CAS Registry No. 267656-07-05; Jun. 1, 2000.
CAS Registry No. 206881-97-2; Jun. 11, 1998.
CAS Registry No. 206881-93-8; Jun. 11, 1998.
CAS Registry No. 185105-91-3; Jun. 17, 1997.
CAS Registry No. 185105-81-1; Jan. 16, 1997.
CAS Registry No. 185105-80-0; Jan. 16, 1997.
CAS Registry No. 185105-62-8; Jan. 16, 1997.
CAS Registry No. 185105-61-7; Jan. 16, 1997.
CAS Registry No. 185105-58-2; Jan. 16, 1997.
CAS Registry No. 185105-57-1; Jan. 16, 1997.
CAS Registry No. 185105-56-0; Jan. 16, 1997.
CAS Registry No. 185105-44-6; Jan. 16, 1997.
CAS Registry No. 185105-40-2; Jan. 16, 1997.
CAS Registry No. 185105-31-1; Jan. 16, 1997.
CAS Registry No. 185105-30-0; Jan. 16, 1997.
CAS Registry No. 143886-38-8; Oct. 9, 1992.
CAS Registry No. 134502-79-7; Jun. 28, 1991.
CAS Registry No. 100395-15-1; Feb. 22, 1986.
CAS Registry No. 99989-49-8; Feb. 1, 1986.
CAS Registry No. 89790-55-6; Nov. 16, 1984.
CAS Registry No. 89790-53-4; Nov. 16, 1984.
Chan, O.H., et al. Evaluation of a Targeted Prodrug Strategy to Enhance Oral Absorption of Poorly Water-Soluable Compounds. Parmaceutical Research. 1998. 15(7):1012-1018.
Dall'Igna, O.P., et al. Neuroprotection by caffeine and adenosine A 2A receptor blockade of β-amyloid neurotoxicity. Br. J. Pharmacol. 2003. 138:1207-1209.
El Yacoubi, M., et al. Adenosine A 2A receptor antagonists are potential antidepressants: evidence based on pharmacology and A 2A receptor knockout mice. Br. J. Pharmacol. 2001. 134:68-77.
Gondi, S.R. and Son, D.Y. Synthesis of N,N'-bis(2-Thiazolinyl)-, N,N'bis(2-Thiazolyl)-, and N,N'-bis (2-Pyrimidinyl)-Benzene Dicarboxamides. Synthetic Communications. 2004.
Ikeda, K., et al. Neuroprotection by adenosine A 2A receptor blockade in experimental models of Parkinson's disease. J. Neurochem. 2002. 80:262-270.
Impagnatiello, F., et al. Adenosine receptors in neurological disorders. Emerging Therapeutic Targets. 2000. 4(5):635-664.
Jacobson, K.A. and Gao, Z.-G. Adenosine receptors as therapeutic targets. Nature Reviews: Drug Discovery. Mar. 2006. 5:247-264.
King, F.D. ed. Medicinal Chemistry: Principles and Practice. The Royal Society of Chemistry. Cambridge, GB. 1994. pp. 206-225.
Kumar, S., et al. Syntheses and Anthelmintic Activity of Alkyl 5(6)-(Substituted-carbamoyl)- and 5(6)-(Disubstituted-carbamoyl)benzimidazole-2-carbamates and Related Compounds. J. Med. Chem. 1984. 27(8):1083-1089.
Methippara, M.M., et al. Effects on Sleep of Microdialysis of Adenosine A1 and A2A Receptor Analogs into the Lateral Preoptic Area of Rats. Am. J. Physiol. Regul. Integr. Comp. Physiol. 2005. 289:R1715-R1723.
Monopoli, A., et al. Blockade of adenosine A 2A receptors by SCH 58261 results in neuroprotective effects in cerebral ischaemia in rats. NeuroRepor. Dec. 1998. 9(17):3955-3959.
Nagel, J., et al. Effects of an Adenosine A 2A Receptor Blockade in the Nucleus Accumbens on Locomotion, Feeding, and Prepulse Inhibition in Rats. Synapse. 2003. 49:279-286.
Ongini, E., et al. Dual Actions of A 2A Adenosine Receptor Antagonists on Motor Dysfunction and Neurodegenerative Processes. Drug Dev. Res. 2001. 52:379-386.
Ongini, E., et al. Adenosine A 2A Receptors and Neuroprotection. Annals of NY Academy of Sciences. 1997. 825(1):30-48.
Prediger, R.D.S., et al. Blockade of Adenosine A2A Receptors Reverses Short-Term Social Memory Impairments in Spontaneously Hypertensive Rats. Behay. Brain Res. 2005. 159:197-205.
Richardson, P.J., et al. Adenosine A 2A receptor antagonists as new agents for the treatment of Parkinson's disease. TiPS. Sep. 1997. 18:338-344.
Sauer, R., et al. Water-Soluable Phosphate Prodrugs of 1-Propargyl-8-styrylxanthine Derivatives, A 2A-Selective Adenosine Receptor Antagonists. J. Med. Chem. 2000. 43(3):440-448.
Svenningsson, P., et al. Distribution, Biochemistry and Function of Striatal Adenosine A 2A Receptors. Progress in Neurobiology. 1999. 59:355-396.
van Muijlwijk-Koezen, J.E., et al. Thiazole and Thiadiazole Analogues as a Novel Class of Adenosine Receptor Antagonists. J. Med. Chem. 2001. 44(5):749-762.
Guttman, M., et al. Current Concepts in the diagnosis and management of Parkinson's disease. CMAJ. Feb. 4, 2003. 168(3):293-301.
Thomas, B. and Beal, M.F. Parkinson's disease. Human Molecular Genetics. 2007. 16(2):R183-R194.
Guttman et al., Canadian Medical Association Journal, Feb. 4, 2003, 168(3), pp. 293-301.

SEQUENCE LISTING

```
<160> NUMBER OF SEQ ID NOS: 2

<210> SEQ ID NO 1
<211> LENGTH: 33
<212> TYPE: DNA
<213> ORGANISM: Homo sapiens

<400> SEQUENCE: 1

tttacgcgtg gccatgccca tcatgggctc ctc                                33


<210> SEQ ID NO 2
<211> LENGTH: 30
<212> TYPE: DNA
<213> ORGANISM: Homo sapiens

<400> SEQUENCE: 2

tttctagaat caggacactc ctgctccatc                                    30
```

2-ACYLAMINOTHIAZOLE DERIVATIVES

This application is a §371 national stage of PCT International Application No. PCT/DK2005/000591, filed Sep. 20, 2005 on behalf of H. Lundbeck A/S, which claims priority of Danish Application No. PA 200401441, filed Sep. 22, 2004, and U.S. Provisional Application No. 60/612,236 filed Sep. 22, 2004, the contents of all of which are hereby incorporated by reference into the subject application.

This application hereby incorporates by reference the Sequence Listing submitted in Computer Readable Form as file 11663054_SequenceListing.txt created on Sep. 24, 2008 (578 bytes).

FIELD OF THE INVENTION

The compounds of the present invention belong to a novel class of 2-acylamino-thiazole derivatives having affinity for the adenosine 2A ($A_{2A}$) receptor. The compounds are $A_{2A}$-receptor ligands, such as antagonists, agonists, reverse agonists or partial agonists, and are useful in the treatment of neurological and psychiatric disorders where an $A_{2A}$-receptor is implicated. Examples of diseases where am $A_{2A}$-receptor is implicated are Parkinson's Disease (PD), Alzheimer's Disease, Huntington's disease, cerebral ischemia, haemorrhagic stroke, neonatal ischemia and hypoxia, subarachnoid hemorrhage, traumatic brain injury, cardiac arrest, Multiple Sclerosis, depression and psychosis.

BACKGROUND OF THE INVENTION

Adenosine is present in all cells, including neurons and glia, of mammalian organisms where it modulates a variety of important physiological processes. The action of adenosine is mediated by specific receptors, which belong to the family of G protein-coupled receptors. Four adenosine receptors have been cloned and characterized, $A_1$, $A_{2A}$, $A_{2B}$ and $A_3$ (Fredholm et al, 1994, *Pharmac. Rev.*, 46, 143-156). The main intracellular signaling pathways involve the formation of cAMP, with $A_1$ and $A_3$ receptors causing inhibition of adenylate cyclase and $A_{2A}$ and $A_{2B}$ receptors activating it (Olah et al, *Pharacol. Ther.*, 2000, 85, 55-75).

All of the adenosine receptors have been located in the CNS (Impagnatiell O et al, *Emerg. Ther. Targets*, 2000, 4, 635-644; Rosin et al, *J. Comp. Neurol.*, 1998, 401, 163-186). The receptor of interest here, $A_{2A}$, is predominantly found in dopamine-rich areas, such as the basal ganglia components; the striatum and the globus pallidus, in various mammalians, including humans. The basal ganglia, with the striatum as a central component, are involved in integration of cortical, thalamic and limbic information to produce motor behaviours (for review see Svenningson et al, *Prog. Neurobiol.*, 1999, 59, 355-396).

In the striatum $A_{2A}$ and dopamine $D_2$ receptors are found closely co-localized on the striatopallidal GABAergic neurons, forming the so-called indirect output pathway from the striatum, which is involved in motor inhibition. $A_{2A}$ receptors contribute to control of motor behaviour by modulating the neurotransmission of GABA, dopamine, acetylcholine and glutamate in various ways. Currently, the interactions between $A_{2A}$ and $D_2$ receptors, and especially the actions of $A_{2A}$ antagonists, is of great interest in the treatment for Parkinson's disease (PD). The $A_{2A}$ receptors interact tonically and antagonistically with the $D_2$ receptors, causing a decrease in affinity of the $D_2$ receptors for dopamine upon stimulation. Thus, $A_{2A}$ antagonists may be capable of enhancing the effect of endogenous dopamine as well as clinically used dopamine agonists and increase the time-period of dopaminergic drug response. (For details and references therein see e.g: Richardson et al, *Trends Pharmacol. Sci.*, 1997, 18, 338-344; Svenningson et al, *Prog. Neurobiol.*, 1999, 59, 355-396; Fuxe et al, *Parkinson's Dis. Adv.*, 2001, 86, 345-353).

Selective $A_{2A}$ receptor agonists and antagonists have been widely described in pharmacological, behavioural and neuroprotective experiments in rodents and non-human primates (for reviews see: Richardson et al, *Trends Pharmacol. Sci.*, 1997, 18, 338-344; Ribeiro et al, *Prog. Neurobiol.*, 2003, 68, 377-392; Ongini et al, *Il Farmaco*, 2001, 56, 87-90; Wardas, *Polish J Pharmacology*, 2003, 54, 313-326).

The close interaction of $D_2$ and $A_{2A}$ receptors can be clearly exemplified in models of catalepsy, where $D_2$ receptor antagonists as well as $A_{2A}$ receptor agonists induce catalepsy, which is counteracted by $A_{2A}$ receptor antagonists and $D_2$ receptor agonists, respectively (see Svenningson et al, *Prog. Neurobiol.*, 1999, 59, 355-396 and references therein).

Promising anti-parkinsonian effects of $A_{2A}$ receptor antagonists have currently been reported by many investigators. For example, both SCH58261 (2-(2-furanyl)-7-(2-phenylethyl)-7H-pyrazolo[4,3-e][1,2,4]triazolo[1,5-c]pyrimidin-5-amine) and KW-6002 (8-[(1E)-2-(3,4-dimethoxyphenyl)ethenyl]-1,3-diethyl-3,7-dihydro-7-methyl-1H-purine-2,6-dione), enhance contralateral rotations, elicited by a subthreshold dose of levodopa, in unilateral 6-OHDA (6-hydroxydopamine) lesioned mice and rats (See Ongini et al, *Drug Dev. Res.*, 2001, 52, 379-386 and references therein). Furthermore, KW-6002 significantly improves motor impairment induced in non-human primates by MPTP (1-methyl-4-phenyl-1,2,3,6-tetrahydropyridine), without causing dyskinesias, that is commonly described for long-term treatment with the dopamine agonist L-dopa (Kanda et al, *Ann. Neurol.*, 1998, 43, 507-513; Grondin et al, Neurology, 1999, 52, 1673-1677; Kanda et al, *Exp. Neurol.*, 2000, 162, 321-327).

Thus, $A_{2A}$ receptor antagonists show great potential as future drugs for long-term medication of PD patients, since they do not only reverse the motor impairment but also can slow down or stop the progress of the disease by promoting cell survival.

Neuroprotective effects by $A_{2A}$ receptor antagonists have recently been reported in in vivo and in vitro models of different neurodegenerative diseases (for review see: Wardas J., *Pol. J. Pharmacol.* 2002, 54, 313-26 and Stone T W. *Adv. Exp. Med. Biol.* 2002, 513, 249-80). $A_{2A}$ antagonists have been shown to be neuroprotective in different PD models like in MPTP treated mice and 6-OHDA-lesioned rats. Here, KW-6002 prevented functional loss of dopaminergic nerve terminals in the striatum as well as prevented gliosis normally induced around degenerating neurons (Ikeda et al, *J. Neurochem.*, 2002, 80, 262-270; Hirsch et al, *Adv. Neurol.*, 1999, 80, 9-18; Kanda et al, *Ann. Neurology*, 2000, 43 (4), 507-513, Lundblad et al. *J. Neurochem.* 2003, 84(6), 1398-410). Similar results have been obtained in experimental models of Huntington's disease (HD). In rat HD models quinolinic acid or kainate induced lesions were reduced after using adenosine $A_{2A}$ receptor antagonists, with a decrease in striatal cell loss and motor changes (Reggio et al, *Brain Res.* 1999, 831, 315-318; Popoli et al, *J. Neurosci.*, 2002, 22, 1967-1975). In addition, it has been shown that $A_{2A}$ receptor antagonists decrease neuronal cell death after cerebral ischemia in neonatal and adult rats and gerbils (Gao Y, Phillis J W., *Life Sci.* 1994, 55(3), PL61-5; Monopoli A. et al, *Neuroreport*, 1998, 9(17), 3955-9). $A_{2A}$ knock out animals have been reported to be protected from neonatal hypoxic ischemia and transient focal ischemia (Bona E. et al, *Neuropharmacology*, 1997, 36(9), 1327-38; Chen J F. et al, *J Neurosci,* 1999, 19(21), 9192-9200) and from 3NP (3-nitropropionic acid) induced, presynaptic, neurotoxic glutamate release (Blum D. et al, *J. Neurosci,* 2003, 23, 5361-5369). The protective effect of $A_{2A}$ antagonists against neurodegeneration by glutamate release have allready been shown in a rat model of ischemic damage to the cerebral cortex (Simpson R E, *J Neurochem,* 1992, 58, 1683-1690 and O'Regan M H. et al, Brain Res, 1992, 582, 22-26).

Protection by $A_{2A}$ antagonists has also been reported in primary astrocytes, in a rat model of bFGF induced astrogliosis, an amyloid beta peptide 25-35 induced neurotoxicity in cerebral granule cells (CGCs) and model of QA induced neuronal cell death in rat organotypic slice cultures (Brambilla R. et al. *Glia.* 2003, 43, 190-194; Dall'Igna O P. et al. *Br. J. Pharmacol.* 2003, 138:1207-1209; Tebano M T, et al. gEur. J. Pharmacol. 2002, 253-257)

Collectively, $A_{2A}$ receptor antagonists can efficiently protect different neurons from various forms of insult induced neurodegeneration (Abbracchio M P, Cattabeni F 1999 *Ann. NY Acad. Sci.* 890: 79-92; Ongini E. et al, *Ann. NY Acad. Sci.,* 1997, 825: 30-48).

Adenosine and its analogues induce "depressant-like" effects in animal models of psychiatric disorders (Minor et al., *Behav. Neurosci.,* 1994, 108: 265-276; Woodson et al., *Behav. Neurosci.* 1998, 112: 399-409). Moreover, these behavioural deficits were found to be reversed by adenosine $A_{2A}$ receptor antagonists (Minor et al., *Behav. Brain Res.* 2001, 120, 230-212). Further studies have shown that treatment with adenosine or 2-chloroadenosine increased immobility time in the mouse forced swimming test, another animal model of depression generally considered reliable (Porsolt et al., *Arch. Int. Pharmacodyn. Ther.,* 1977, 229: 327-336).

Several compounds with dual affinity for $A_{2A}$ and $A_1$ receptor subtypes, known as the 4-amino[1,2,3]triazolo[4,3-a]quinoxalines, has been shown to be active in the rat forced swimming test (Sarges et al., *J. Med. Chem.,* 1990, 33, 2240-2254) indicating antidepressant activity of the substances. Most recently, $A_{2A}$ receptor knockout mice were found to be less sensitive to "depressant" challenges than their wildtype littermates (El Yacoubi et al., *Br. J. Pharmacol.* 2001, 134, 68-77). Consistent with this data, the $A_{2A}$ receptor antagonists SCH58261 and KW6002 reduced the total immobility time in the mouse tail suspension test (El Yacoubi et al., *Br. J. Pharmacol.* 2001, 134, 69-77). The antagonists SCH58261 and ZM241385 4-(2-[7-amino-2-(2-furyl)[1,2,4]triazolo[2,3-a][1,3,5]triazin-5-ylamino]-ethyl)phenol were also found to reduce immobility when administered to mice previously screened for having high immobility timne, while SCH58261 reduced immobility of mice that were selectively bred for their "helplessness" in this model (El Yacoubi et al., *Br. J. Pharmacol.* 2001, 134, 68-77).

Studies using $A_{2A}$ knockout mice suggest that these animals show a blunted response to psychostirnulants such as amphetamine and cocaine, despite the fact that their expression and binding affinities of D1 and D2 receptors are unaffected (Chen et al., *Neurosci.,* 2000, 97, 195-204). Moreover, inactivation of $A_{2A}$ receptors has been shown to selectively attenuate amphetamine-induced behavioural sensitisation (Chen et al., *Neuropsychopharmacol.,* 2003, 28, 1086-1095). In addition, $A_{2A}$ knockout mice show reduced startle and PPI of the acoustic startle (Wang et al., *Behav. Brain Res.,* 2003, 143, 201-207), measures often used to detect antipsychotic activity. Further support is found in studies where pharmacological blockade of $A_{2A}$ receptors with a selective antagonist completely abolished pre-pulse imhibition (PPI) (Nagel et al., Synapse, 2003, 49, 279-286). Psychostimulants, such as MK-801 and amphetamine failed to disr-upt startle and PPI in $A_{2A}$ KO mice (Wang et al., *Behav. Brain Res.,* 2003, 143, 201-207).

Thus, the available evidence suggests that adenosine $A_{2A}$ receptor antagonists, by specifically modulating mesostriatal or mesocorticolimbic dopaminergic pathways, may possess antidepressant and/or antipsychotic properties WO02/42298 discloses compounds of the formula:

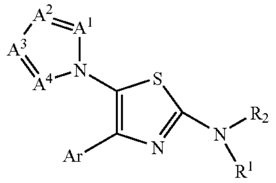

as $A_{2B}$ receptor antagonists which in general selectively inhibit activation of the $A_{2b}$ receptor over the adenosine $A_1$ and $A_{2A}$ receptors. The compounds are disclosed as being useful in the treatment of inflammatory or obstructive airways diseases.

Hence, there is a desire for novel $A_{2A}$-receptor ligands, such as antagonists, agonists, reverse agonists or partial agonists.

SUMMARY OF THE INVENTION

The objective of the present invention is to provide compounds that are $A_{2A}$-receptor ligands, such as antagonists, agonists, reverse agonists or partial agonists.

Accordingly, the present invention relates to compounds of formula I

I

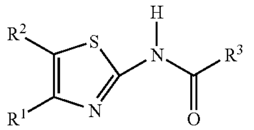

wherein $R^1$ is phenyl, thien-2-yl or thien-3-yl, wherein each phenyl and thienyl optionally are substituted with one or more substituents selected from halogen, $C_{1-6}$-alkyl and $C_{1-6}$-alkoxy;

$R^2$ is a five membered heteroaryl selected from the group consisting of furan-2-yl, furan-3-yl, [1,2,4]-oxadiazol-3-yl, [1,2,4]-oxadiazol-5-yl, [1,2,5]-oxadiazol-3-yl, [1,2,4]-thiadiazol-3-yl, [1,2,4]-thiadiazol-5-yl, [1,2,5]-thiadiazol-3-yl, wherein the heteroaryl is optionally substituted with one or more substituents selected from the group consisting of $C_{1-6}$-alkyl, phenyl-$C_{1-6}$-alkyl, $C_{1-6}$-alkoxy and $C_{1-6}$-alkoxy-$C_{1-6}$-alkyl, or $R^2$ is tetrazol-5-yl substituted in the 1 or 2-position with $C_{1-6}$-alkyl or phenyl-$C_{1-6}$-alkyl or $C_{3-8}$-cycloalkyl-$C_{1-6}$-alkyl, or $R^2$ is 5-oxo-4,5-dihydro-[1,3,4]-oxadiazol-2-yl;

and $R^3$ is selected from the group consisting of $C_{1-6}$-alkyl, $C_{3-8}$-cycloalkyl, $C_{3-8}$-cyclo-alkyl-$C_{1-6}$-alkyl, furanyl, furanyl-$C_{1-6}$-alkyl, thienyl, thienyl-$C_{1-6}$-alkyl, phenyl, phenyl-$C_{2-6}$-alkene and phenyl-$C_{1-6}$-alkyl wherein the phenyl-$C_{1-6}$-alkyl optionally is substituted in the phenyl ring with one or more substituents selected from halogen, $C_{1-6}$-alkyl and $C_{1-6}$-alkoxy;

for use as a medicament.

In a second aspect the present invention relates to the use of compounds of formula I as defined above for the manufacture of a medicament for treatment of a disease where an $A_{2A}$-receptor is implicated.

In a third aspect the present invention relates to compounds of formula I as defined above provided that the compound is not N-[5-(5-nitro-furan-2-yl)-4-phenyl-thiazol-2-yl]-benzamide.

The compounds of the invention are $A_{2A}$-receptor ligands, such as antagonists, agonists, reverse agonists or partial agonists having a human $A_{2A}$ binding affinity ($K_i$) of 5 μM or less, typically of 1 μM or less, preferably of 550 nM or less, more preferred of 200 nM or less, even more preferred of 50 nM or less and most preferred of 10 nM or less.

DETAILED DESCRIPTION OF THE INVENTION

In a particular embodiment the present invention relates to use of compounds of formula I as defined above for the manufacture of a medicament for the treatment of a disease where an $A_{2A}$-receptor is implicated, is selected from the group consisting of Parkinson's Disease, Alzheimer's Disease, Huntington's disease, cerebral ischemia, haemorrhagic stroke, neonatal ischemia and hypoxia, subarachnoid haemorrhage, traumatic brain injury, cardiac arrest, Multiple Sclerosis, depression and psychosis.

In a more particular embodiment the present invention relates to use of such compounds for the manufacture of a medicament for the treatment of Parkinson's Disease.

In a particular embodiment the present invention relates to such compounds which are $A_{2A}$-receptor antagonists.

In another particular embodiment the compounds are selective ligands to the $A_{2A}$ receptor over the $A_1$ or $A_{2B}$ receptors. In a more particular embodiment the compounds are selective ligands to the $A_{2A}$ receptor over the $A_1$ receptor. In an equally particular embodiment the compounds are selective ligands to the $A_{2A}$ receptor over the $A_{2B}$ receptor.

In a particular embodiment the present invention relates to compounds of formula I as defined above wherein $R^1$ is phenyl.

In another particular embodiment the present invention relates to compounds of formula I as defined above wherein $R^1$ is thien-2-yl.

In another particular embodiment the present invention relates to compounds of formula I as defined above wherein if $R^2$ is a tetrazol-5-yl, then it is substituted in the 2-position.

In another particular embodiment the present invention relates to compounds of formula I as defined above wherein if $R^2$ is a tetrazol-5-yl, then it is substituted in the 1-position.

In a more particular embodiment the present invention relates to compounds of formula I as defined above wherein if $R^2$ is a tetrazol-5-yl, then it is substituted with methyl, ethyl, propyl, butyl, isobutyl, cyclopropanmethyl or plhenethyl.

In another particular embodiment the present invention relates to compounds of formula I as defined above wherein $R^2$ is furan-2-yl or furan-3-yl, wherein the heteroaryl is optionally substituted with on or more substituents selected from the group consisting of $C_{1-6}$-alkyl, phenyl-$C_{1-6}$-alkyl, $C_{1-6}$-alkoxy and $C_{1-6}$-alkoxy-$C_{1-6}$-alkyl.

In another particular embodiment the present invention relates to compounds of formula I as defined above wherein $R^2$ is [1,2,4]-oxadiazol-3-yl, wherein the heteroaryl is optionally substituted with on or more substituents selected from the group consisting of $C_{1-6}$-alkyl, phenyl-$C_{1-6}$-alkyl, $C_{1-6}$-alkoxy and $C_{1-6}$-alkoxy-$C_{1-6}$-alkyl.

In another particular embodiment the present invention relates to compounds of formula I as defined above wherein $R^2$ is [1,2,4]-oxadiazol-5-yl, wherein the heteroaryl is optionally substituted with on or more substituents selected from the group consisting of $C_{1-6}$-alkyl, phenyl-$C_{1-6}$-allyl, $C_{1-6}$-alkoxy and $C_{1-6}$-alkoxy-$C_{1-6}$-alkyl.

In another particular embodiment the present invention relates to compounds of formula I as defined above wherein $R^2$ is [1,2,5]-oxadiazol-3-yl, wherein the heteroaryl is optionally substituted with on or more substituents selected from the group consisting of $C_{1-6}$-alkyl, phenyl-$C_{1-6}$-alkyl, $C_{1-6}$-alkoxy and $C_{1-6}$-alkoxy-$C_{1-6}$-alkyl.

In another particular embodiment the present invention relates to compounds of formula I as defined above wherein $R^2$ is 5-oxo-4,5-dihydro-[1,3,4]-oxadiazol-2-yl.

In a particular embodiment the present invention relates to compounds of fcormula I as defined above wherein $R^3$ is selected from the group consisting of $C_{1-6}$-alkyl, $C_{3-8}$-cycloalkyl, $C_{3-8}$-cycloalkylmethyl, furan-2-yl, furan-3-yl, thien-2-yl, thien-2-yl-methyl, thien-3-yl, phenylmethyl, phenethylene and benzyl optionally substituted in the phenyl ring.

In a more particular embodiment the present invention relates to compounds of formula I as defined above wherein the benzyl is substituted with one or two methoxy groups in the phenyl ring.

In an equally particular embodiment the present invention relates to compounds of formula I as defined above wherein the benzyl is substituted in the 3 and/or 4 position of the phenyl ring, for use as a medicament.

In a particular embodiment the present invention relates to compounds of formula I as defined above selected from the group consisting of:

2-(3,4-Dimethoxy-phenyl)-N-[5-(2-ethyl-2H-tetrazol-5-yl)-4-phenyl-thiazol-2-yl]-acetamide, 2-(3,4-dimethoxy-phenyl)-N-(5-[1,2,4]oxadiazol-3-yl-4-phenyl-thiazol-2-yl)-acetamide, N-(5-furan-3-yl-4-phenyl-thiazol-2-yl)-isobutyramide, cyclopropanecarboxylic acid [5-(2-ethyl-2H-tetrazol-5-yl)-4-phenyl-thiazol-2-yl]-amide, furan-3-carboxylic acid [5-(2-ethyl-2H-tetrazol-5-yl)-4-phenyl-thiazol-2-yl]-amide, N-[5-(2-ethyl-2H-tetrazol-5-yl)-4-phenyl-thiazol-2-yl]-isobutyramide, furan-2-carboxylic acid [5-(2-ethyl-2H-tetrazol-5-yl)-4-phenyl-thiazol-2-yl]-amide, cyclohexanecarboxylic acid [5-(2-ethyl-2H-tetrazol-5-yl)-4-phenyl-thiazol-2-yl]-amide, 2-cyclopentyl-N-[5-(2-ethyl-2H-tetrazol-5-yl)-4-phenyl-thiazol-2-yl]-acetamide, N-[5-(2-ethyl-2H-tetrazol-5-yl)-4-phenyl-thiazol-2-yl]-propionamide, cyclopropanecarboxylic acid (5-[1,2,4]oxadiazol-3-yl-4-phenyl-thiazol-2-yl)-amide, thiophene-3-carboxylic acid [5-(2-ethyl-2H-tetrazol-5-yl)-4-phenyl-thiazol-2-yl]-amide, 2-cyclopentyl-N-(5-[1,2,4]oxadiazol-3-yl-4-phenyl-thiazol-2-yl)-acetamide, furan-3-carboxylic acid [5-(2-phenethyl-2H-tetrazol-5-yl)-4-phenyl-thiazol-2-yl]-amide, N-(5-furan-2-yl-4-phenyl-thiazol-2-yl)-isobutyramide, furan-2-carboxylic acid (5-furan-3-yl-4-phenyl-thiazol-2-yl)-amide, 2-(3,4-dimethoxy-phenyl)-N-(5-furan-2-yl-4-phenyl-thiazol-2-yl)-acetamide, cyclopropanecarboxylic acid (5-furan-3-yl-4-phenyl-thiazol-2-yl)-amide, 2-(3-methoxy-phenyl)-N-(5-[1,2,4]oxadiazol-3-yl-4-phenyl-thiazol-2-yl)-acetamide,
2-(3-methoxy-phenyl)-N-[5-(2-phenethyl-2H-tetrazol-5-yl)-4-phenyl-thiazol-2-yl]-acetamide,
N-(5-furan-2-yl-4-phenyl-thiazol-2-yl)-2,2-dimethyl-propionamide,
N-(5-furan-3-yl-4-phenyl-thiazol-2-yl)-propionamide,
N-[5-(2-phenethyl-2H-tetrazol-5-yl)-4-phenyl-thiazol-2-yl]-isobutyramide,
N-(5-furan-2-yl-4-phenyl-thiazol-2-yl)-propionamide,
furan-2-carboxylic acid [5-(2-methyl-2H-tetrazol-5-yl)-4-phenyl-thiazol-2-yl]-amide,
3,3-dimethyl-N-[5-(2-methyl-2H-tetrazol-5-yl)-4-phenyl-thiazol-2-yl]-butyramide,
cyclopropanecarboxylic acid [5-(2-methyl-2H-tetrazol-5-yl)-4-phenyl-thiazol-2-yl]-amide,
2-cyclopentyl-N-[5-(2-methyl-2H-tetrazol-5-yl)-4-phenyl-thiazol-2-yl]-acetamide,
N-[5-(2-methyl-2H-tetrazol-5-yl)-4-phenyl-thiazol-2-yl]-isobutyramide,
3-methyl-N-[5-(2-methyl-2H-tetrazol-5-yl)-4-phenyl-thiazol-2-yl]-butyramide,
N-[5-(2-methyl-2H-tetrazol-5-yl)-4-phenyl-thiazol-2-yl]-propionamide,
N-[5-(2-methyl-2H-tetrazol-5-yl)-4-phenyl-thiazol-2-yl]-2-phenyl-acetamide,
hexanoic acid [5-(2-methyl-2H-tetrazol-5-yl)-4-phenyl-thiazol-2-yl]-amide,
N-[5-(2-methyl-2H-tetrazol-5-yl)-4-phenyl-thiazol-2-yl]-2-thiophen-2-yl-acetamide,
N-[5-(2-methyl-2H-tetrazol-5-yl)-4-phenyl-thiazol-2-yl]-acetamide,
2,2-dimethyl-N-[5-(2-methyl-2H-tetrazol-5-yl)-4-phenyl-thiazol-2-yl]-propionamide,
thiophene-3-carboxylic acid [5-(2-methyl-2H-tetrazol-5-yl)-4-phenyl-thiazol-2-yl]-amide,
N-[4-phenyl-5-(2-propyl-2H-tetrazol-5-yl)-thiazol-2-yl]-isobutyramide,
3-methyl-N-[4-phenyl-5-(2-propyl-2H-tetrazol-5-yl)-thiazol-2-yl]-butyramide,
N-[4-phenyl-5-(2-propyl-2H-tetrazol-5-yl)-thiazol-2-yl]-propionamide,
2-phenyl-N-[4-phenyl-5-(2-propyl-2H-tetrazol-5-yl)-thiazol-2-yl]-acetamide,
N-[4-phenyl-5-(2-propyl-2H-tetrazol-5-yl)-thiazol-2-yl]-2-thiophen-2-yl-acetamide,
N-[4-phenyl-5-(2-propyl-2H-tetrazol-5-yl)-thiazol-2-yl]-acetamide,
2,2-dimethyl-N-[4-phenyl-5-(2-propyl-2H-tetrazol-5-yl)-thiazol-2-yl]-propionamide,
thiophene-3-carboxylic acid [4-phenyl-5-(2-propyl-2H-tetrazol-5-yl)-thiazol-2-yl]-amide,
N-[5-(2-butyl-2H-tetrazol-5-yl)-4-phenyl-thiazol-2-yl]-isobutyramide,
2-cyclopentyl-N-[5-(2-isobutyl-2H-tetrazol-5-yl)-4-phenyl-thiazol-2-yl]-acetamide,
N-[5-(2-isobutyl-2H-tetrazol-5-yl)-4-phenyl-thiazol-2-yl]-2-thiophen-2-yl-acetamide,
N-[5-(2-cyclopropylmethyl-2H-tetrazol-5-yl)-4-phenyl-thiazol-2-yl]-3-methyl-butyramide,
furan-2-carboxylic acid [5-(3-methyl-[1,2,4]oxadiazol-5-yl)-4-phenyl-thiazol-2-yl]-amide,
3,3-dimethyl-N-[5-(5-methyl-[1,2,4]oxadiazol-3-yl)-4-phenyl-thiazol-2-yl]-butyramide,
N-[5-(3-methyl-[1,2,4]oxadiazol-5-yl)-4-phenyl-thiazol-2-yl]-benzamide,
N-[5-(3-ethyl-[1,2,4]oxadiazol-5-yl)-4-phenyl-thiazol-2-yl]-benzamide,
N-[5-(5-methyl-[1,2,4]oxadiazol-3-yl)-4-phenyl-thiazol-2-yl]-benzamide,
cyclopropanecarboxylic acid [5-(3-methyl-[1,2,4]oxadiazol-5-yl)-4-phenyl-thiazol-2-yl]-amide,
cyclopropanecarboxylic acid [5-(3-ethyl-[1,2,4]oxadiazol-5-yl)-4-phenyl-thiazol-2-yl]-amide,
cyclopropanecarboxylic acid [5-(5-methyl-[1,2,4]oxadiazol-3-yl)-4-phenyl-thiazol-2-yl]-amide,
cyclopropanecarboxylic acid [5-(5-ethyl-[1,2,4]oxadiazol-3-yl)-4-phenyl-thiazol-2-yl]-amide,
2-cyclopentyl-N-[5-(3-methyl-[1,2,4]oxadiazol-5-yl)-4-phenyl-thiazol-2-yl]-acetamide,
2-cyclopentyl-N-[5-(3-ethyl-[1,2,4]oxadiazol-5-yl)-4-phenyl-thiazol-2-yl]-acetamide,
2-cyclopentyl-N-[5-(5-methyl-[1,2,4]oxadiazol-3-yl)-4-phenyl-thiazol-2-yl]-acetamide,
2-cyclopentyl-N-[5-(5-ethyl-[1,2,4]oxadiazol-3-yl)-4-phenyl-thiazol-2-yl]-acetamide,
cyclohexanecarboxylic acid [5-(3-methyl-[1,2,4]oxadiazol-5-yl)-4-phenyl-thiazol-2-yl]-amide,
cyclohexanecarboxylic acid [5-(3-ethyl-[1,2,4]oxadiazol-5-yl)-4-phenyl-thiazol-2-yl]-amide,
cyclohexanecarboxylic acid [5-(5-methyl-[1,2,4]oxadiazol-3-yl)-4-phenyl-thiazol-2-yl]-amide,
N-[5-(1-methyl-1H-tetrazol-5-yl)-4-phenyl-thiazol-2-yl]-isobutyramide,
N-[5-(3-ethyl-[1,2,4]oxadiazol-5-yl)-4-phenyl-thiazol-2-yl]-isobutyramide,
3-methyl-N-[5-(3-methyl-[1,2,4]oxadiazol-5-yl)-4-phenyl-thiazol-2-yl]-butyramide,
N-[5-(3-ethyl-[1,2,4]oxadiazol-5-yl)-4-phenyl-thiazol-2-yl]-3-methyl-butyramide,
3-methyl-N-[5-(5-methyl-[1,2,4]oxadiazol-3-yl)-4-phenyl-thiazol-2-yl]-butyramide,
N-[5-(3-methyl-[1,2,4]oxadiazol-5-yl)-4-phenyl-thiazol-2-yl]-propionamide,
N-[5-(3-ethyl-[1,2,4]oxadiazol-5-yl)-4-phenyl-thiazol-2-yl]-propionamide,
N-[5-(5-methyl-[1,2,4]oxadiazol-3-yl)-4-phenyl-thiazol-2-yl]-propionamide,
N-[5-(3-methyl-[1,2,4]oxadiazol-5-yl)-4-phenyl-thiazol-2-yl]-2-phenyl-acetamide,
N-[5-(3-ethyl-[1,2,4]oxadiazol-5-yl)-4-phenyl-thiazol-2-yl]-2-phenyl-acetamide,
N-[5-(5-methyl-[1,2,4]oxadiazol-3-yl)-4-phenyl-thiazol-2-yl]-2-phenyl-acetamide,
N-[5-(5-Oxo-4,5-dihydro-[1,3,4]oxadiazol-2-yl)-4-phenyl-thiazol-2-yl]-2-phenyl-acetamide,
2-(3,4-dimethoxy-phenyl)-N-[5-(2-methyl-2H-tetrazol-5-yl)-4-thiophen-2-yl-thiazol-2-yl]-acetamide,
N-[5-(5-ethyl-[1,2,4]oxadiazol-3-yl)-4-phenyl-thiazol-2-yl]-3-phenyl-acrylamide,
hexanoic acid [5-(3-methyl-[1,2,4]oxadiazol-5-yl)-4-phenyl-thiazol-2-yl]-amide,
hexanoic acid [5-(5-methyl-[1,2,4]oxadiazol-3-yl)-4-phenyl-thiazol-2-yl]-amide,
N-[5-(3-methyl-[1,2,4]oxadiazol-5-yl)-4-phenyl-thiazol-2-yl]-2-thiophen-2-yl-acetamide,
N-[5-(3-ethyl-[1,2,4]oxadiazol-5-yl)-4-phenyl-thiazol-2-yl]-2-thiophen-2-yl-acetamide,
N-[5-(5-methyl-[1,2,4]oxadiazol-3-yl)-4-phenyl-thiazol-2-yl]-2-thiophen-2-yl-acetamide,
N-[5-(3-methyl-[1,2,4]oxadiazol-5-yl)-4-phenyl-thiazol-2-yl]-acetamide, N-[5-(3-ethyl-[1,2,4]oxadiazol-5-yl)-4-phenyl-thiazol-2-yl]-acetamide, N-[5-(5-methyl-[1,2,4]oxadiazol-3-yl)-4-phenyl-thiazol-2-yl]-acetamide, 2,2-dimethyl-N-[5-(3-methyl-[1,2,4]oxadiazol-5-yl)-4-phenyl-thiazol-2-yl]-propionamide, N-[5-(3-ethyl-[1,2,4]oxadiazol-5-yl)-4-phenyl-thiazol-2-yl]-2,2-dimethyl-propionamide, 2,2-dimethyl-N-[5-(5-methyl-[1,2,4]oxadiazol-3-yl)-4-phenyl-thiazol-2-yl]-propionamide, furan-3-carboxylic acid [5-(2-methyl-2H-tetrazol-5-yl)-4-thiophen-2-yl-thiazol-2-yl]-amide, thiophene-3-carboxylic acid [5-(3-methyl-[1,2,4]oxadiazol-5-yl)-4-phenyl-thiazol-2-yl]-amide, thiophene-3-carboxylic acid [5-(5-methyl-[1,2,4]oxadiazol-3-yl)-4-phenyl-thiazol-2-yl]-amide.

The compounds of the general formula I may exist as optical isomers thereof and such optical isomers are also embraced by the invention. Throughout the specification and claims, reference to specific compounds refers to the racemates unless otherwise indicated.

The term $C_{1-6}$-alkyl refers to a branched or unbranched alkyl group having from one to six carbon atoms inclusive, such as methyl, ethyl, 1-propyl, 2-propyl, 1-butyl, 2-butyl, 2-methyl-2-propyl, and 2-methyl-1-propyl.

The term $C_{3-8}$-cycloalkyl designates a monocyclic or bicyclic carbocycle having three to eight C-atoms, such as cyclopropyl, cyclopentyl, cyclohexyl, etc.

Halogen means fluoro, chloro, bromo or iodo.

As used herein, the term acyl refers to a formyl, $C_{1-6}$-alkylcarbonyl, arylcarbonyl, aryl-$C_{1-6}$-alkylcarbonyl, $C_{3-8}$-cycloalkylcarbonyl or a $C_{3-8}$-cycloalkyl-$C_{1-6}$-alkyl-carbonyl group.

The terms $C_{1-6}$-alkoxy, $C_{3-8}$-cycloalkyl-$C_{1-6}$-alkyl, phenyl-$C_{1-6}$-alkyl, heteroaryl-$C_{1-6}$-alkyl, $C_{1-6}$-alkylamino, $C_{1-6}$-alkylcarbonyl, and the like, designate such groups in which the $C_{1-6}$-alkyl, aryl, heteroaryl and the $C_{3-8}$-cycloalkyl group are as defined above.

The term $C_{2-6}$-alkene refers to a branched or unbranched alkene group having from two to six carbon atoms inclusive, such as ethylene, 1-propylene, 2-propylene, isopropylene, methylpropylene, 1-butylene, 2-butylene and 3-butylene.

The term furanyl refers to furan-2-yl or furan-3-yl.

The term thienyl refers to thien-2-yl or thien-3-yl.

The term aryl refers to a carbocyclic aromatic group, such as phenyl or naphthyl, in particular phenyl.

The term heteroaryl refers to 5-membered monocyclic rings such as 1H-tetrazolyl, 3H-1,2,3-oxathiazolyl, 3H-1,2,4-oxathiazolyl, 3H-1,2,5-oxathiazolyl, 1,3,2-oxathiazolyl, 1,3,4-oxathiazolyl, 1,4,2-oxathiazolyl, 3H-1,2,4-dioxazolyl, 1,3,2-dioxazolyl, 1,4,2-dioxazolyl, 3H-1,2,3-dithiazolyl, 3H-1,2,4-dithiazolyl, 1,3,2-dithiazolyl, 1,4,2-dithiazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1H-1,2,3-triazolyl, 1H-1,2,4-triazolyl, isoxazolyl, oxazolyl, isothiazolyl, thiazolyl, 1H-imidazolyl, 1H-pyrazolyl, 1H-pyrrolyl, furanyl, thienyl, 1H-pentazole; 6-membered monocyclic rings such as 1,2,3-oxathiazinyl, 1,2,4-oxathiazinyl, 1,2,5-oxathiazinyl, 4H-1,3,5-oxathiazinyl, 1,4,2-oxathiazinyl, 1,4,3-oxathiazinyl, 1,2,3-dioxazinyl, 1,2,4-dioxazinyl, 4H-1,3,2-dioxazinyl, 4H-1,3,5-dioxazinyl, 1,4,2-dioxazinyl, 2H-1,5,2-dioxazinyl, 1,2,3-dithiazinyl, 1,2,4-dithiazinyl, 4H-1,3,2-dithiazinyl, 4H-1,3,5-dithiazinyl, 1,4,2-dithiazinyl, 2H-1,5,2-dithiazinyl, 2H-1,2,3-oxadiazinyl, 2H-1,2,4-oxadiazinyl, 2H-1,2,5-oxadiazinyl, 2H-1,2,6-oxadiazinyl, 2H-1,3,4-oxadiazinyl, 2H-1,3,5-oxadiazinyl, 2H-1,2,3-thiadiazinyl, 2H-1,2,4-thiadiazinyl, 2H-1,2,5-thiadiazinyl, 2H-1,2,6-thiadiazinyl, 2H-1,3,4-thiadiazinyl, 2H-1,3,5-thiadiazinyl, 1,2,3-triazinyl, 1,2,4-triazinyl, 1,3,5-triazinyl, 2H-1,2-oxazinyl, 2H-1,3-oxazinyl, 2H-1,4-oxazinyl, 2H-1,2-thiazinyl, 2H-1,3-thiazinyl, 2H-1,4-thiazinyl, pyrazinyl, pyridazinyl, pyrimidyl, pyridyl, 2H-pyranyl, 2H-thiinyl; and to bicyclic rings such as 3H-1,2,3-benzoxathiazolyl, 1,3,2-benzodioxazolyl, 3H-1,2,3-benzodithiazolyl, 1,3,2-benzodithiazolyl, benzfurazanyl, 1,2,3-benzoxadiazolyl, 1,2,3-benzothiadiazolyl, 2,1,3-benzothiadiazolyl, 1H-benzotriazolyl, 1,2-benzisoxazolyl, 2,1-benzisoxazolyl, benzoxazolyl, 1,2-benzisothiazolyl, 2,1-benzisothiazolyl, benzothiazolyl, 1H-benzimidazolyl, 1H-indazolyl, 3H-1,2-benzoxathiolyl, 1,3-benzoxathiolyl, 3H-2,1-benzoxathiolyl, 3H-1,2-benzodioxolyl, 1,3-benzodioxolyl 3H-1,2-benzodithiolyl, 1,3-benzodithiolyl, 1H-indolyl, 2H-isoindolyl, benzofuranyl, isobenzofuranyl, 1-benzothienyl, 2-benzothienyl, 1H-2,1-benzoxazinyl, 1H-2,3-benzoxazinyl, 2H-1,2-benzoxazinyl, 2H-1,3-benzoxazinyl, 2H-1,4-benzoxazinyl, 2H-3,1-benzoxazinyl, 1H-2,1-benzothiazinyl, 1H-2,3-benzothiazinyl, 2H-1,2-benzothiazinyl, 2H-1,3-benzothiazinyl, 2H-1,4-benzothiazinyl, 2H-3,1-benzothiazinyl, cinnolinyl, phtalazinyl, quinazolinyl, quinoxalinyl, isoquinolyl, quinolyl, 1H-2-benzopyranyl, 2H-1-benzopyranyl, 1H-2-benzothiopyranyl or 2H-1-benzothiopyranyl.

The term rac means racemic.

The acid addition salts of the compounds of the invention are pharmaceutically acceptable salts formed with non-toxic acids. Exemplary of such organic salts are those with maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

The pharmaceutical compositions of this invention, or those which are manufactured in accordance with this invention, may be administered by any suitable route, for example orally in the form of tablets, capsules, powders, syrups, etc., or parenterally in the form of solutions for injection. For preparing such compositions, methods well known in the art may be used, and any pharmaceutically acceptable carriers, diluents, excipients or other additives normally used in the art may be used.

Conveniently, the compounds of the invention are administered in unit dosage form containing said compounds in an amount of about 0.01 to 100 mg.

The total daily dose is usually in the range of about 0.05-500 mg, and most preferably about 0.1 to 50 mg of the active compound of the invention.

The compounds of the invention are prepared by the following general methods:

Coupling of a compound with formula II wherein $R^1$ and $R^2$ are as described above, with an activated carboxylic acid $R^3$—COOH or carboxylic acid chloride $R^3$—COCl or anhydride $R^3$—CO—O—CO—$R^3$, wherein $R^3$ is as defined above.

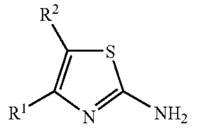

II

The coupling of compounds of formula II with carboxylic acids, $R^3$—COOH, is performed by standard procedures known to chemists skilled in the art e.g. in the presence of a carbodiimide coupling reagent at temperatures between 20-80° C. in a suitable polar or apolar solvent such as 1-methyl-2-pyrrolidinone or 1,2-dichloroethane, or coupling of a starting material of formula II with carboxylic acid chlorides, $R^3$—COCl, or anhydrides, $R^3$—CO—O—CO—$R^3$, in the presence of a suitable base such as pyridine at temperatures between 20-60° C. in a suitable solvent such as 1,2-dichloroethane.

The compounds of formula II were prepared according to procedures known to chemists skilled in the art or as exemplified in scheme A.

Scheme A

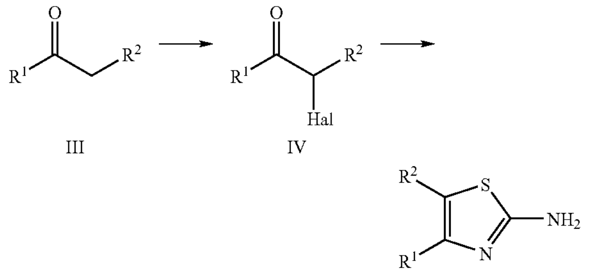

III IV II

Compounds of formula III can be prepared by literature procedures (Aicart et al., J. Heterocycl. Chem., 1985, 22, 921-925; Chakrasali et al., Synthesis, 1988, EN; 6, 453-455) or by methods known to the chemist skilled in the art. The furan analogue 3-(2-phenyl-[1,3]dithian-2-ylmethyl)-furan can for example be prepared by metalation of 2-phenyl-[1,3]dithiane (Kamal et al. *Tetrahedron Lett.* 2002, 43, 1347) with a suitable metalation agent such as n-butyllithium (Lipshutz et al. *Tett Lett.,* 1990, 31, 7261) and subsequent reaction with 3-bromomethyl-furan (Mateos et al. *J. Org. Chem.,* 1995, 60 3580). Deprotection with for example N-bromosuccinimide or HgO/$HgCl_2$ will give 3-(2-phenyl-[1,3]dithian-2-ylmethyl)-furan. When $R^2$ is 1-alkyl tetrazole or 2-alkyl tetrazole, III can be synthesised according to procedures known to chemists skilled in the art. Starting from 3-oxo-3-phenyl-propionitrile, the nitrile can be converted into the tetrazole by standard procedures. This includes the of an azide as sodium azide and triethylammoniumchloride in a suitable solvent e.g. toluene or DMF at temperatures between 80-120° C. Alkylation of the tetrazole by an alkylating agent such as ethylbromide in the presence of a base such as potassium carbonate and a solvent such as acetone at temperatures between 20-80° C. gives a mixture of the 2-(1-alkyl-2H-tetrazol-5-yl)-1-phenyl-ethanone and 2-(2-alkyl-2H-tetrazol-5-yl)-1-phenyl-ethanone. These two compounds can be separated by chromatographic methods.

Compounds of formula III were halogenated a to the carbonyl group by reaction with $SO_2Cl_2$, $Br_2$ or 12 in a suitable solvent such as 1,2-dichloroethane, diethylether or chloroform. The halogenated products (IV) were then ring closed to the aminothiazoles of formula II by reaction with thiourea in a solvent such as ethanol at a suitable temperature e.g. 20-100° C.

Compounds of formula IIa can be prepared from a compound of formula V (Scheme B). Compound V can be prepared by literature procedures (in analogy to compound prepared by Benjamin. et al., *J. Med. Chem.,* 1983, 26, 100-103) or by the method described above starting from 3-oxo-3-phenyl-propionitrile followed by protection of the amine by a suitable protecting group. 2-Amino-4-phenyl-thiazole-5-carbonitrile can be reacted in a suitable solvent such as ethanol/water with hydroxylamine hydrochlorid in the presence of a suitable base such as potassium or sodium carbonate at a temperature between 50-100° C. to give the amidooxime (VI). The 1,2,4-oxadiazoles (VII) can then be prepared by acylation of the amidooxime for example by acid chlorides or acid anhydrides or by reaction with trimethyl- or triethylorthoformate in the presence of a Lewis acid such as $BF_3$-$Et_2O$ and subsequent dehydration. Removal of the protecting group gives IIa. Alternatively no protecting group is used and by acylation of the amidooxime (for example by acid chlorides or acid anhydrides or by reaction with trimethyl- or triethylorthoformate in the presence of a Lewis acid such as $BF_3$-$Et_2O$ and subsequent dehydration) compound VII where PG is the acyl group from the acid chloride or acid anhydride used. Removal of the protecting group gives IIa.

Scheme B

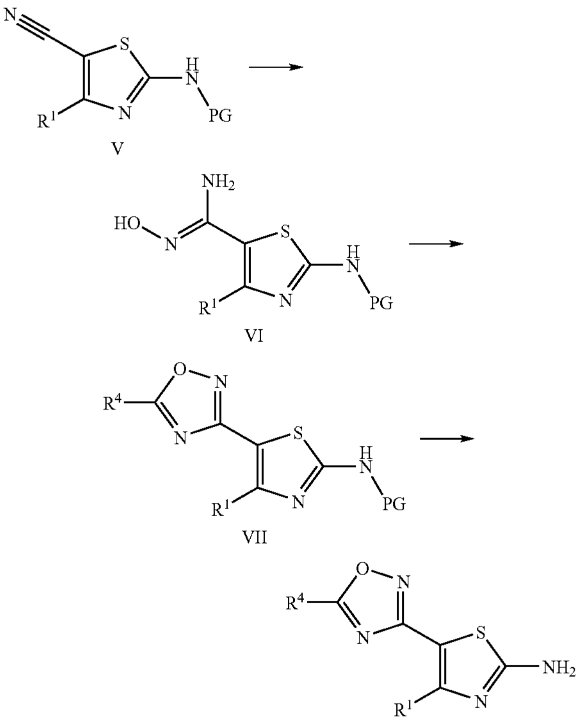

V VI VII IIa $R^4$ = alkoxy

Compounds of formula IIb can be prepared from a compound of formula VIII (Scheme C). Compounds of formula VIII can be prepared by literature procedures (in analogy to compound prepared by Choudhari et al. *J. Indian. Cheep. Soc.,* 1978, 55, 401) or by the method described above from compounds of formula II where R2 is an carboxylic acid ester. Protection of the amine by a suitable protection group (PG) as for example boc (t-butoxycarbonyl) will result in the compound IX. The ester can then be converted into the [1,2,4]-oxadialole by my methods known to the chemist skilled in the art, as for example by reaction with amidooximes in presence of a suitable base such as sodium hydride or pyridine at a temperature between 25° C. and 100° C. Removal of the protecting group gives IIb.

Scheme C

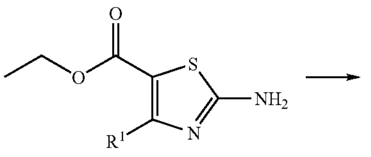

VIII

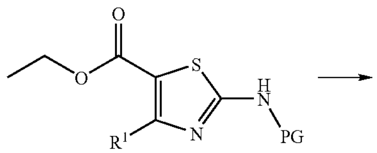

IX

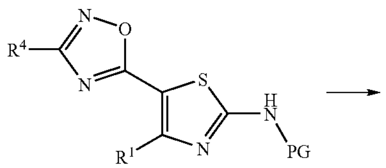

x

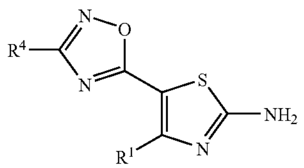

IIb

Compounds of formula IIc can be prepared from compounds of formula VIII (Scheme D). The ester group in the compound of formula VIII can be converted to a hydrazide group by methods known to chemists skilled in the art, as for example by reaction with hydrazine in a suitable solvent such as methanol at a suitable temperature between 25 and 65° C. to give a compound of formula XI. The oxadiazolone ring can then be formed by methods known to chemists skilled in the art. This includes reaction of an hydrazide of formula XI with carbonyldiimidazole or carbonyl dichloride in the presence of a suitable base such as triethylamine in a solvent such as tetrahydrofurane and at temperatures between 25 and 50° C.

Scheme D

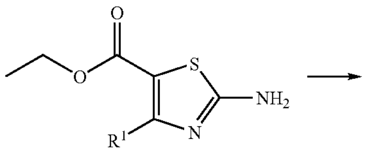

VIII

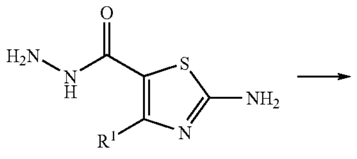

XI

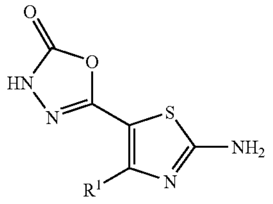

IIc

Experimental Section

Analytical LC-MS data were obtained on a PE Sciex API 150EX instrument equipped with an IonSpray source and a Shimadzu LC-8A/SLC-10A LC system. Column: 30×4.6 mm Waters Symmetry C18 column with 3.5 μm particle size; solventsysteim: A=water/trifluoroacetic acid (100:0.05) and B=water/acetonitrile/trifluoroacetic acid (5:95:0.03); method: Linear gradient elution with 90% A to 100% B in 4 min arnd with a flow rate of 2 ml/min.

Preparative LC-MS-purification was performed on the same instrument. Column: 10×50 mm Waters Symmetry C18 with 5 μm particle size; Method: Linear gradient elution with 30% to 100% B in 7 min and then 30% B in 1 min and with a flow rate of 5.7 mL/min. Fraction collection was performed by split-flow MS detection.

Purity was determined by integration of the UV (254 nm) and ELSD traces. The retention times (RT) are expressed in minutes.

$^1$H NMR spectra were recorded at 500.13 MHz on a Bruker Avance DRX500 instrument or at 250.13 MHz on a Bruker AC 250 instrument or at 400 MHz on a Bruker instrument. Deuterated chloroform (99.8% D) or dimethyl sulfoxide (99.8% D) were used as solvents. TMS was used as internal reference standard. Chemical shift values are expressed in ppm. The following abbreviations are used for multiplicity of NMR signals: s=singlet, d=doublet, t=triplet, q=quartet, qui=quintet, h=heptet, dd=double doublet, dt=double triplet, dq=double quartet, tt=triplet of triplets, m=multiplet, br s=broad singlet and br=broad signal.

For column chromatography silica gel of the type Kieselgel 60, 40-60 mesh ASTM (or $Al_2O_3$ (active, manufacturer: Qualigens India Ltd)) was used. Microwave heated experiments were performed with a Personal Chemistry Emrys Synthesiser or a Personal Chemistry Emrys Optimiser.

EXAMPLES

Preparation of Intermediates

1-Phenyl-2-(2H-tetrazol-5-yl)-ethanone (intermediate for 5-(2-ethyl-2H-tetrazol-5-yl)-4-phenyl-thiazol-2-ylamine)

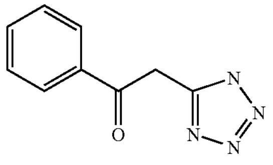

3-Oxo-3-phenyl-propionitrile (6.5 g, 45 mmol), sodium azide (3.3 g, 50 mmol) and triethylammonium chloride (6.7 g, 50 mmol) were stirred in dry toluene (100 mL) under argon at 90° C. for 18 h. A two-phase system was formed. The reaction mixture was cooled and extracted with NaOH (2M, 2×50 mL). The aqueous solution was poured into hydrochloric acid (4M, 200 mL) and the crude product precipitated and was filtered off and recrystalliced from acetonitrile. Yield: 74%.

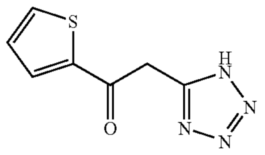

2-(1H-Tetrazol-5-yl)-1-thiophen-2-yl-ethanone

A mixture of 2-thenoylacetonitrile (9 g, 59.3 mmol), Sodium azide (4.33 g, 66.7 mmol) and triethylammonium-chloride (9.14 g, 66.9 mmol) was stirred in dry toluene (139 mL) under argon atmosphere at 90° C. for 18 hrs. A two-phase system was formed, cooled and extracted with NaOH (2M, 3×500 mL), and the aqueous solution was poured into hydrochloric acid (4M, 300 mL) and the crude tetrazole was filtered off and recrystalised from acetonitrile. Yield: 43.5%.

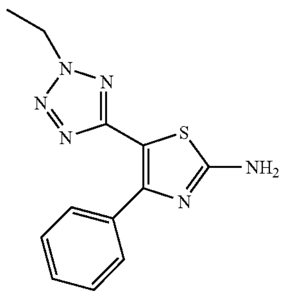

5-(2-Ethyl-2H-tetrazol-5-yl)-4-phenyl-thiazol-2-ylamine

1-Phenyl-2-(2H-tetrazol-5-yl)-ethanone (3.3 g, 17.5 mmol), ethyl iodide (1.4 g, 17.5 mmol) and potassium carbonate (2.4 g, 17.5 mmol) was heated at reflux in acetone (50 mL) for 5 h under argon. The reaction mixture was then poured into water, made acidic with 6M HCl and extracted with diethyl ether. The organic extract was dried and evaporated to a red/orange oil. The oil was dissolved in diethyl ether (100 mL) and bromine (17.5 mmol) was added. The mixture was stirred over night at ambient temperature, then the solvent was removed in vacuo and the residue was redissolved in ethanol (100 mL). Thiourea (35 mmol) was added, and the resulting mixture was heated at reflux for 10 min., after which a solid precipitated. The reaction mixture was poured into water containing NaOH (17.5 mmol), and the orange crude product was recovered by filtration. The crude product was recrystallized from acetonitrile to give pale yellow solid. Yield: 0.6 g, 17%.

$^1H$ NMR ($d_6$-DMSO) (250 MHz): δ 7.65-7.61 (m, 2H), 7.54 (s br, 2H, NH2), 7.38-7.32 (m, 3H), 4.63 (q, 2H), 1.48 (t, 3H).

The following compounds were prepared analogously:

5-(2-Phenethyl-2H-tetrazol-5-yl)-4-phenyl-thiazol-2-ylamine $^1H$ NMR ($d_6$-DMSO): δ 7.6-7.5 (m, 4H); 7.35-7.3 (m, 3H); 7.25 (t, 2H); 7.16 (m, 1H); 7.1 (d, 2H) 4.90 (t, 2H); 3.22 (t, 2H).

5-(2-Methyl-2H-tetrazol-5-yl)-4-phenyl-thiazol-2-ylamine $^1H$ NMR ($d_6$-DMSO) (400 Mhz): δ 7.62 (m, 2H); 7.54 (s, 2H); 7.36-7.33 (m, 3H); 4.29 (s, 3H).

4-Phenyl-5-(2-propyl-2H-tetrazol-5-yl)-thiiazol-2-ylamine $^1H$ NMR ($CDCl_3$) (400 Mhz): δ 7.70 (m, 2H); 7.40 (m, 3H); 6.20-5.80 (br, 2H) 4.51 (t, 2H); 2.01 (m, 2H); 0.96 (t, 3H).

5-(2-Butyl-2H-tetrazol-5-yl)-4-phenyl-thiazol-2-ylamine $^1H$ NMR ($CDCl_3$) (400 Mhz): δ 7.70 (m, 2H); 7.40 (m, 3H); 6.20-5.80 (br, 2H) 4.55 (t, 2H); 1.99-1.91 (m, 2H); 1.40-1.31 (m, 2H); 0.96 (t, 3H).

5-(2-Isobutyl-2H-tetrazol-5-yl)-4-phenyl-thiazol-2-ylamine $^1H$ NMR (MeOD) (400 Mhz): δ 7.57 (m, 2H); 7.36 (m, 3H); 4.41 (d, 2H); 2.26 (m, 1H); 0.93 (d, 6H).

5-(2-Cyclopropylmethyl-2H-tetrazol-5-yl)-4-phenyl-thiazol-2-ylamine $^1H$ NMR (MeOD) (400 Mhz): δ 7.61 (m, 2H); 7.37 (m, 3H); 4.45 (d, 2H); 1.37 (m, 1H); 0.67-0.62 (m, 2H); 0.48-0.44 (m, 2H).

5-(2-Methyl-2H-tetrazol-5-yl)-4-thiophen-2-yl-thiazol-2-ylamine

Prepared from 2-(1H-tetrazol-5-yl)-1-thiophen-2-yl-ethanone and MeI and thiourea.

$^1$H NMR ($d_6$-DMSO) (400 Mhz): δ 8.29 (d, 1H); 7.64 (s, 2H); 7.57 (d, 1H); 7.12 (t, 1H); 4.41 (s, 3H).

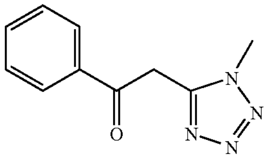

2-(1-Methyl-1H-tetrazol-5-yl)-1-phenyl-ethanone

1-Phenyl-2-(2H-tetrazol-5-yl)-ethanone (13.24 g, 70.4 mmol) was dissolved in acetone (300 mL). MeI (4.6 mL, 73.9 mmol) and $KCO_3$ (10.68 g, 77.4 mmol) were added and the reaction mixture was heated to reflux for 30 min. The reaction mixture was filtered and the solvent was removed in vacuo. The crude product contains a mixture of 2-(1-methyl-1H-tetrazol-5-yl)-1-phenyl-ethanone and 2-(2-methyl-2H-tetrazol-5-yl)-1-phenyl-ethanone. The two compounds were separated by flash column chromatography using ethyl acetate/hexane (6/4) as eluent. 2-(1-Methyl-1H-tetrazol-5-yl)-1-phenyl-ethanone was obtained as a white solid. Yield: 34%.

$^1$H NMR ($d_6$-DMSO) (500 MHz): δ 8.09 (d, 2H), 7.73 (t, 1H), 7.60 (t, 2H), 5.05 (s, 2H), 4.00 (s, 3H).

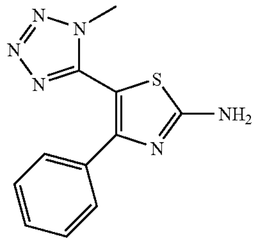

5-(1-Methyl-1H-tetrazol-5-yl)-4-phenyl-thiazol-2-ylamine 2-(1-Methyl-1H-tetrazol-5-yl)-1-phenyl-ethanone (4.9 g, 24.2 mmol) was dissolved in 1,2-dichloroethane (150 mL) and ether (100 mL). Brom (1.24 mL, 24.2 mmol) was added. The reaction mixture was stirred at room temperature for 1 h. the solvent was removed in vacuo. The remenance was dissolved in ethanol (250 mL). Thiourea (3.67 g, 48.5 mmol) was added and the reaction mixture was heated at reflux for 20 min. The reaction mixture was poured into water/ice. Concentrated NaOH (aq) was added until pH=10. The mixture was filtered and the solid product was recrystallised from ethylacetate/hexane. Yield: 58%.

$^1$H NMR ($d_6$-DMSO) (500 MHz): δ 7.7 (s, 2H), 7.35 (m, 3H), 7.25 (m, 2H), 3.5 (s, 3H).

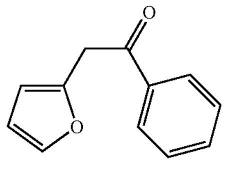

2-Furan-2-yl-1-phenyl-ethanone (intermediate for 5-furan-2-yl-4-phenyl-tliazol-2-ylamine)

2-Furan-2-yl-3-oxo-3-phenyl-propionic acid ethyl ester, prepared as described by Dorsch J. B. and McElvain S. M., *J Am. Chem. Soc* 1932, 54, 2960-2963; (10.0 g, 39 mmol) was dissolved in N-methylpyrrolidin-2-one (13 mL) and acetic acid (3.9 mL) and lithium chloride (4.7 g, 110 mmol) was added. The reaction mixture was heated at reflux for 7 h, then saturated aqueous $NaHCO_3$ was added and the mixture was extracted with diethyl ether. The organic extracts were dried over sodium sulfate, filtered, concentrated in vacuo and purified by flash column chromatography using 1% ethyl acetate in hexane as eluent. Yield: 6.2 g, 85%.

$^1$H NMR ($CDCl_3$) (400 Mhz): δ 8.00 (m, 2H); 7.56 (m, 1H); 7.46 (m, 2H); 7.36 (m, 1H); 6.33 (q, 1H); 6.23 (q, 1H); 4.31 (s, 2H).

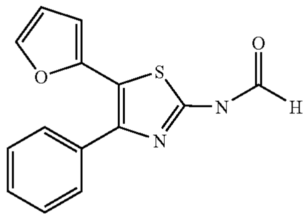

N-(5-Furan-2-yl-4-phenyl-thiazol-2-yl)-formamide (Intermediate for 5-furan-2-yl-4-phenyl-thiazol-2-ylamine)

2-Furan-2-yl-1-phenyl-ethanone (14.0 g, 75 mmol) and thiourea (11.5 g, 150 mmol) was dissolved in DMF (30 mL) and iodine (19.1 g, 75 mmol) was added. The reaction mixture was heated at 100° C. overnight, then diluted with water, made alkaline with saturated aqueous $NH_4OH$, and extracted with ether. The organic phases were washed with water, dried over sodium sulfate, filtered, concentrated and purified by flash column chromatography using 1% ethyl acetate in hexane as eluent. Yield: 9.2 g, 45%

$^1$H NMR ($CDCl_3$) (400 MHz): δ 7.57 (m, 2H); 7.50 (m, 3H); 7.44 (s, 1H); 7.38 (m, 1H); 6.28 (m, 1H); 6.20 (s, 1H).

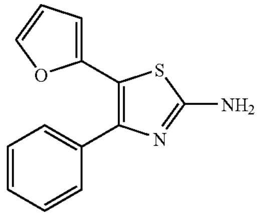

5-Firan-2-yl-4-phenyl-thiazol-2-ylamine

N-(5-Furan-2-yl-4-phenyl-thiazol-2-yl)-formamide (3.9 g, 14.5 mmol) was dissolved in a mixture of methanol (45 mL) and THF (62 mL), and added dropwise HCl (conc.) (6 mL). The reaction mixture was stirred over night and the solvent was evaporated. The residue was extracted with ethyl acetate, and washed with $NaHCO_3$ (aq.; sat.), then washed with water, dried over sodium sulfate and concentrated in vacuo. The crude product was purified on neutral $Al_2O_3$ using 30-35% ethyl acetate in hexane as eluent. Yield: 2.6 g, 76%.

$^1$H NMR ($CDCl_3$) (400 MHz): δ 7.54 (m, 2H); 7.33 (m, 4H); 6.32 (q, 1H); 6.17 (q, 1H); 5.45 (br s, 2H).

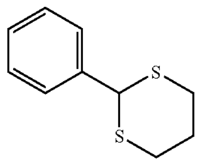

2-Phenyl-[1,3]dithiane (intermediate for 5-furan-3-yl-4-phenyl-thiazol-2-ylamine)

To a solution of benzaldehyde (15.0 g, 141 mmol) in chloroform (150 mL), propane-1,3-dithiol (16.9 g, 155 mmol) and boron trifluoride etherate (26.1 g, 183 mmol) were added. The reaction mixture was stirred at ambient temperature for 24 h, and was then poured into ice-cold aqueous sodium hydroxide (10%) and extracted with chloroform. The combined chloroform extracts were washed with water, dried over sodium sulfate, concentrated and purified by flash column chromatography using 1% ethyl acetate in hexane as eluent. Yield: 21.2 g, 77%.

$^1$H NMR ($CDCl_3$) (400 MHz): δ 7.46 (m, 2H); 7.30 (m, 3H); 5.16 (s, 1H); 3.06 (m, 2H); 2.90 (m, 2H); 2.17 (m, 1H); 1.93 (m, 1H).

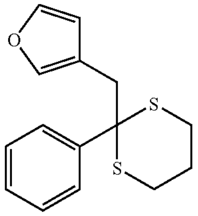

3-(2-Phenyl-[1,3]dithian-2-ylmethyl)-furan (Intermediate for 5-furan-3-yl-4-phenyl-thiazol-2-ylamine)

A stirred suspension of sodium tert-butoxide (5.16 g, 54 mmol) in dry hexane (120 mL) was added n-butyl lithium (34 mL, 51 mmol) at 0° C. and stirred for 1 h at 0° C., and then for 1 h at room temperature. The mixture was cooled to −78° C., and transferred to a preformed mixture of 2-phenyl-[1,3] dithiane (10.0 g, 51 mmol) dissolved in dry THF (120 mL) at −78° C., and n-butyl lithium (34 mL, 51 mmol) and kept for 15 min. A dark brown colored solution was observed. After stirring for 1 h at −78° C., 3-bromomethyl-furan (Danso-Danquah R. E. and Scott A. I. *Tetrahedron,* 1993, 49, 8195-8210; New D. G. et al, *J. Org. Chem.,* 1996, 61, 1578-1598) (10.7 g, 66 mmol) was added via canula. After 30 min., the reaction mixture was quenched with water and warmed to ambient temperature. The reaction mixture was extracted with diethyl ether, and the organic extracts were dried over sodium sulfate and concentrated. The crude product was purified by flash column chromatography using 0.2-0.5% ethyl acetate in hexane as eluent. Yield: 5.6 g, 32%.

$^1$H NMR ($CDCl_3$) (400 MHz): δ 7.79 (m, 2H); 7.33 (m, 2H); 7.26 (m, 1H); 7.17 (m, 1H); 6.92 (m, 1H); 5.73 (s, 1H); 3.11 (s, 2H); 2.68 (m, 4H); 1.93 (m, 2H).

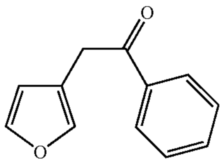

2-Furan-3-yl-1-phenyl-ethanone (intermediate for 5-furan-3-yl-4-phenyl-thiazol-2-ylamine)

3-(2-Phenyl-[1,3]dithian-2-ylmethyl)-furan (11.5 g, 41 mmol) was suspended in 9:1 methanol/water (v/v) (150 mL) with slight heating. A solution of $HgCl_2$ (22.3 g, 82 mmol) in methanol/water (50 mL) and solid HgO (8.0 g, 36.9 mmol) was added, and the mixture was heated at reflux under a nitrogen atmosphere for 6-7 h. The reaction mixture was filtered through celite to remove solids, and then concentrated. The resulting aqueous mixture was extracted with ethyl acetate, the combined organic extracts were washed with water, dried over sodium sulfate, and evaporated. The crude product was purified by flash column chromatography using 2% ethyl acetate in hexane as eluent. Yield: 5.7 g, 75%.

$^1$H NMR ($CDCl_3$) (400 MHz): δ 8.00 (m, 2H); 7.57 (s, 1H); 7.47 (m, 2H); 7.39 (m, 2H); 6.36 (s, 1H); 4.11 (s, 2H).

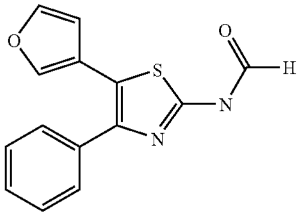

N-(5-Furan-3-yl-4-phenyl-thiazol-2-yl)-formamide (Intermediate for 5-furan-3-yl-4-phenyl-thiazol-2-ylamine)

To a solution of 2-furan-3-yl-1-phenyl-ethanone (5.7 g, 31 mmol) and thiourea (4.7 g, 61 mmol) in DMF (57 mL) was and added iodine (7.8 g, 31 mmol). The reaction mixture was heated at 100° C. overnight, then it was diluted with water and made alkaline with saturated aqueous $NH_4OH$, and extracted with ether. The organic phases were washed with water, dried over sodium sulfate, concentrated and purified on neutral $Al_2O_3$ using 50% ethyl acetate in hexane as eluent. Yield: 5.7 g, 69%.

GC-MS ($M^+$) 270

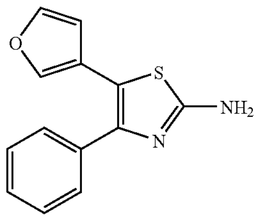

5-Furan-3-yl-4-phenyl-thiazol-2-ylamine

N-(5-Furan-3-yl-4-phenyl-thiazol-2-yl)-formamide (5.7 g, 21 mmol) was dissolved in a mixture of methanol (210 mL) and THF (90 mL), and conc. squeous hydrochloric acid (8.7 mL) was added dropwise at room temperature. The reaction mixture was stirred over night and the solvent was removed by evaporation. The residue was extracted with ethyl acetate, and washed with $NaHCO_3$ (aq.; sat.) and water and dried over sodium sulfate. The solvent was removed and the crude product was purified on neutral $Al_2O_3$ using 30-35% ethyl acetate in hexane as eluent. Yield: 2.5 g, 49%.

$^1H$ NMR ($CDCl_3$) (400 MHz): δ 7.53 (m, 2H); 7.38 (q, 1H); 7.31 (m, 4H); 6.19 (m, 1H); 5.26 (br s, 2H).

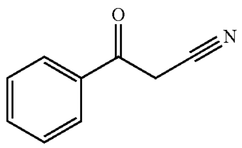

3-Oxo-3-phenylpropionitril (Intermediate for 5-[1,2,4]oxadiazol-3-yl-4-phenyl-thiazol-2-ylamine)

Ethyl benzoate (20 g, 133 mmol) and NaOMe (133 mmol, from 3 g Na) in methanol was mixed and heated with stirring to 80° C. until a homogeneous gelatinous mass had formed. Acetonitrile (6.8 g, 165 mmol) was then added slowly under the surface of this mass over a period of 30 min. The temperature was raised to 120° C. and heated at reflux for 24 h, and the reaction mixture was then cooled on an ice bath and treated with water and diethyl ether until the solid material had dissolved. The aqueous layer was separated and acidified with 5% $H_2SO_4$, washed with $NaHCO_3$ (aq; sat.), dried over sodium sulfate and concentrated. The crude product was used in the next reaction without any further purification. Yield: 7.3 g, 37.8%.

$^1H$ NMR ($CDCl_3$) (400 MHz): δ 7.91 (m, 2H); 7.66 (m, 1H); 7.51 (m, 2H); 4.08 (s, 2H).

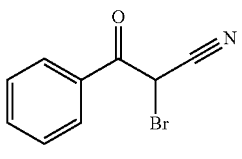

2-Bromo-3-oxo-3-phenylpropionitril (Intermediate for 5-[1,2,4]oxadiazol-3-yl-4-phenyl-thiazol-2-ylamine)

3-Oxo-3-phenylpropionitril (1.5 g, 10 mmol) was dissolved in dry chloroform (10 mL) at 0° C., and pyridine (0.81 mL, 10 mmol) was added. Bromine (4.7 mL, 10 mmol) dissolved in chloroform (4.7 mL) was added dropwise over an hour, then the reaction mixture was heated at 45° C. over night. The reaction mixture was diluted with chloroform and washed with water. The organic phases were dried over sodium sulfate and evaporated to give the crude product, which was used in the next reaction without any further purification.

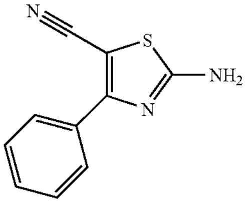

2-Amino-4-phenyl-thiazole-5-carbonitrile (Intermediate for 5-[1,2,4]oxadiazol-3-yl-4-phenyl-thiazol-2-ylamine)

2-Bromo-3-oxo-3-phenylpropionitrile (0.5 g, 3.4 mmol) was mixed with thiourea (0.52 g, 6.8 mmol) and iodine (0.43 g, 3.4 mmol) and the mixture was heated on a steam bath for 12 h. It was then diluted with water and made alkaline with saturated aqueous $NH_4OH$, and extracted with ethyl acetate. The organic phases were washed with water and brine, dried over sodium sulfate, and evaporated to dryness to give the crude product, which was used in the next reaction without any further purification. Yield: 0.2 g, 29%.

$^1H$ NMR ($d_6$-DMSO) (400 MHz): δ 8.26 (s, 2H); 7.91 (m, 2H); 7.50 (m, 3H).

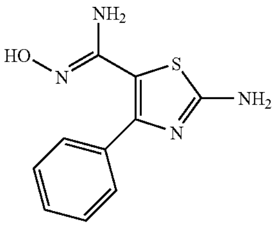

2-Amino-N-hydroxy-4-phenyl-thiazole-5-carboxamidine (Intermediate for 5-[1,2,4]oxadiazol-3-yl-4-phenyl-thiazol-2-ylamine)

2-Amino-4-phenyl-thiazole-5-carbonitrile (0.13 g, 0.6 mmol) was suspended in 1:1 water/ethanol (v/v) (24 mL) and added hydroxylamine hydrochloride (1.47 g, 21 mmol) and potassium carbonate (1.86 g, 13 mmol). The reaction mixture was heated at reflux for 3 days, then the solvent was reduced and the aqueous phase was extracted with dichloromethane. The organic layer was washed with water and brine, and was dried over sodium sulfate. The solvent was evaporated to yield a yellow solid. Yield: 0.1 g, 66%.

$^1$H NMR ($D_6$-DMSO) (400 MHz): δ 9.52 (s, 1H); 7.64 (m, 2H); 7.31 (m, 3H); 7.14 (s, 2H); 5.50 (s, 2H).

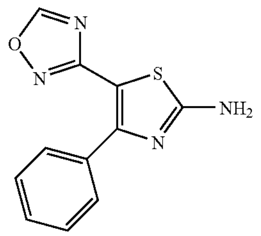

5-[1,2,4]Oxadiazol-3-yl-4-phenyl-thiazol-2-ylamine

2-Amino-N-hydroxy-4-phenyl-thiazole-5-carboxamidine (1.0 g, 4.3 mmol) was dissolved in methanol (20 mL), and trimethyl orthoformate (1.2 mL, 11 mmol) containing boron trifluoride etherate (0.2 mL, 1.6 mmol) was added End the mixture was heated at reflux for 3 h. The reaction mixture was cooled, and the solvent was removed under reduced pressure at 20° C. The residue was extracted with ethyl acetate, and the solution was washed with saturated aqueous $NaHCO_3$ dried over sodium sulfate and evaporated. The crude product was purified by flash column chromatography, eluted with the gradient of 10-18% ethyl acetate in hexanes to get the product (the product was eluted by 18% ethyl acetate in hexanes). Yield: 0.1 g, 10%

$^1$H NMR ($d_6$-DMSO) (400 MHz): δ 9.47 (s, 1H); 7.72 (s, 2H); 7.63 (m, 2H); 7.38 (m, 3H).

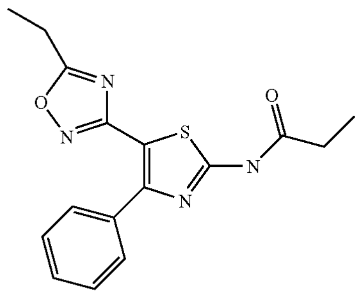

N-[5-(5-Ethyl-[1,2,4]oxadiazol-3-yl)-4-phenyl-thiazol-2-yl]-propionamide

2-Amino-N-hydroxy-4-phenyl-thiazole-5-carboxamidine (1.5 g, 6.4 mmol) was dissolved in dry THF (50 mL). Ethyl-diisopropyl-amine (2.5 mL) and propionylchloride (2.8 mL, 5 eq) was added. The reaction mixture was stirred overnight at room temperature. pH was adjusted to pH ~2 by addition of HCl in ethanol. The reaction mixture was stirred overnight at room temperature. The solvent was evaporated to yield a yellow oil. The crude product was purified by flash column chromatography, eluted with 30% ethyl acetate in hexanes to give the product as a white solid. Yield: 49%.

The following compound was prepared analogously:

N-[5-(5-Methyl-[1,2,4]oxadiazol-3-yl)-4-phenyl-thiazol-2-yl]-acetamide

Prepared from 2-amino-N-hydroxy-4-phenyl-thiazole-5-carboxamidine acetyl chloride.

$^1$H NMR ($CDCl_3$) (500 MHz): δ 11.55 (s, 1H); 7.75 (m, 2H); 7.43 (m, 3H); 2.59 (s, 3H); 1.5 (s, 3H).

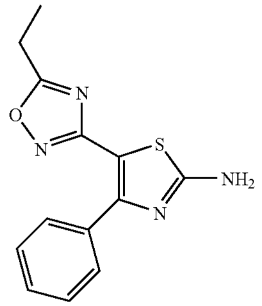

5-(5-Ethyl-[1,2,4]oxadiazol-3-yl)-4-phenyl-thiazol-2-ylamine

N-[5-(5-Ethyl-[1,2,4]oxadiazol-3-yl)-4-phenyl-thiazol-2-yl]-propionamide (1.02 g, 3.1 mmol) was suspended in MeOH (40 mL), konc. HCl(aq) was added and the reaction mixture was heated at refluc for 2 h. Saturated aqueous $NaHCO_3$ (100 mL) was added to the reaction mixture. The aqueous phase was extracted with ethyl acetate (2×75 mL). The organic phase was dried with $MgSO_4$ and the solvent was evaporated to yield white solid. Yield: 91%.

The following compound was prepared analogously:

5-(5-Methyl-[1,2,4]oxadiazol-3-yl)-4-phenyl-thiazol-2-ylamine

Prepared from N-[5-(5-methyl-[1,2,4]oxadiazol-3-yl)-4-phenyl-thiazol-2-yl]-acetamide.

$^1$H NMR ($CDCl_3$) (500 MHz): δ 7.7 (m, 2H); 7.4 (m, 3H); 5.3 (s, 2H); 2.55 (s, 3H).

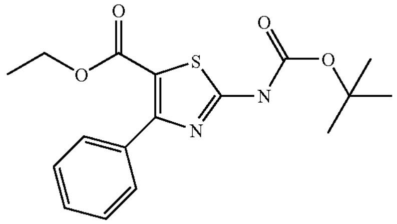

2-tert-Butoxycarbonylamino-4-phenyl-thiazole-5-carboxylic Acid Ethyl Ester

2-Amino-4-phenyl-thiazole-5-carboxylic acid ethyl ester (2 g, 8.1 mmol), was dissolved in THF (50 mL). Triethylamine (25 mL), dimethyl-pyridin-4-yl-amine (0.1 g, 0.8 mmol) and ditert-butil-dicarbonate (2 g, 9.2 mmol) were added. The reaction mixture was stirred overnight. The reaction mixture was filtered and solvents were removed in vacuo. The crude product was purified by flash column chromatography, eluted with the gradient of 0-10% ethyl acetate in hexanes to give the product as a white solid. Yield: 53%.

N-hydroxy-propionamidine

Hydroxyl ammonium chloride (69.5 ml, 1 mol) was dissolved in ethanol. NaOH (Aq, 28%, 110 mL) and propionitrile (71 mL, 1 mol) were added. The reaction mixture was stirred at 40° C. for 48 h. The reaction mixture was filtered. The solvent was removed from the filtrate by evaporation in vacuo. The crude product was purified by flash column chromatography, eluted with the gradient of ethyl acetate/ethanol 9/1 to give the product. Yield: 52%.

The following compound was prepared analogously:

N-hydroxy-acetamidine

Prepared from acetonitrile.

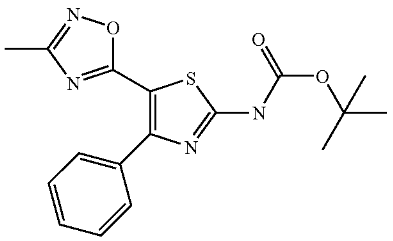

[5-(3-Methyl-[1,2,4]oxadiazol-5-yl)-4-phenyl-thiazol-2-yl]-carbamic Acid tert-butyl ester 2-Tert-butoxycarbonylamino-4-phenyl-thiazole-5-carboxylic acid ethyl ester (1.9 g 5.6 mmol) was dissolved in dry THF (60 mL). Sodium hydride (60% in oil) and N-hydroxy-acetamidine (0.83 g, 11.2 mmol) dissolved in THF (30 mL) was added. The reaction mixture was heated to reflux over night. The reaction mixture was cooled and ethyl acetate (75 mL) glacial acetic acid (0.43 g) were added. The organic mixture was washed with brine (75 mL). The aqueous phase was extracted with ethylacetate The combined organic phases was washed with brine (50 mL) dried with $MgSO_4$ and solvents were removed in vacuo to give a solid. Yield: 36%.

$^1$H NMR ($CDCl_3$) (500 MHz): δ 8.55 (br, 1H); 7.72 (m, 2H); 7.43 (m, 3H); 2.4 (s, 3H); 1.5 (s, 9H).

The following compound was prepared analogously:

[5-(3-Ethyl-[1,2,4]oxadiazol-5-yl)-4-phenyl-thiazol-2-yl]-carbamic acid tert-butyl ester Prepared from 2-tert-butoxycarbonylamino-4-phenyl-thiazole-5-carboxylic acid ethyl ester and N-hydroxy-propionamidine.

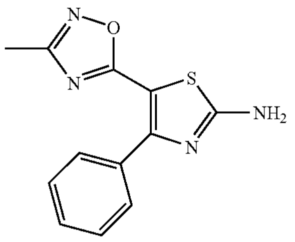

5-(3-Methyl-[1,2,4]oxadiazol-5-yl)-4-phenyl-thiazol-2-ylamine

[5-(3-Methyl-[1,2,4]oxadiazol-5-yl)-4-phenyl-thiazol-2-yl]-carbamic acid tert-butyl ester was suspended in glacial acetic acid (20 mL). TFA (20 mL) was added. The reaction mixture was stirred at room temperature overnight. The reaction mixture was added to brine (100 mL) and pH was adjusted to pH 10 with ammonia. The mixture was extracted with EtOAc (2×75 mL). The combined organic phases was washed with brine (50 mL), dried with $MgSO_4$ and solvents were removed in vacuo to give a white solid. Yield 98%.

$^1$H NMR ($d_6$-DMSO) (500 MHz): δ 8.03 (br, 2H); 7.64 (m, 2H); 7.43 (m, 3H); 2.25 (s, 3H).

The following compound was prepared analogously:

5-(3-Ethyl-[1,2,4]oxadiazol-5-yl)-4-phenyl-thiazol-2-ylamine

Prepared from [5-(3-ethyl-[1,2,4]oxadiazol-5-yl)-4-phenyl-thiazol-2-yl]-carbamic acid tert-butyl ester.

$^1$H NMR ($d_6$-DMSO) (500 MHz): δ 8.03 (br, 2H); 7.64 (m, 2H); 7.43 (m, 3H); 2.67 (q, 2H); 1.18 (t, 3H).

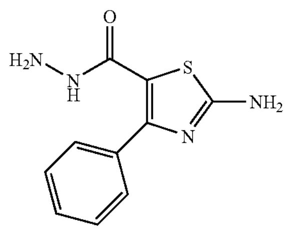

2-Amino-4-phenyl-thiazole-5-carboxylic Acid Hydrazide

2-Amino-4-phenyl-thiazole-5-carboxylic acid ethyl ester (5.0 g, 20 mmol) was suspended in methanol. Hydrazine monohydrate (5 mL, 100 mmol) was added and heated to reflux for 2 h. Hydrazine monohydrate (10 mL) was added and heated to reflux for 48 h. Water (100 mL) was added to the reaction mixture and the methanol was removed by evaporation in vacuo. The product precipitates and the solid product is collected by filtration. Yield: 70%.

$^1$H NMR ($d_6$-DMSO) (500 MHz): δ 8.9 (s, 1H); 7.6 (m, 2H); 7.3 (m, 5H); 4.35 (s, 2H).

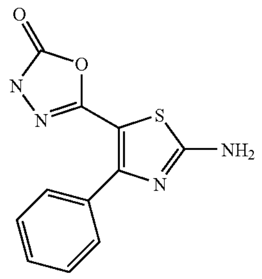

5-(2-Amino-4-phenyl-thiazol-5-yl)-3H-[1,3,4]oxadiazol-2-one

2-Amino-4-phenyl-thiazole-5-carboxylic acid hydrazide (1 g, 4.3 mmol) was suspended in tetrahydrofurane (50 mL). Triethylamine (5 mL, 40 mmol) and carbonyldiimidazole (0.83, 5.1 mmol) was added. The reaction mixture was stirred at room temperature for 1 h. The solvent was removed in vacuo. The crude product was purified by flash column chromatography, eluted with the ethyl acetate/hexanes (1/1) to give the product as a solid. Yield: 20%.

(3,4-Dimethoxy-phenyl)-acetyl Chloride (3,4-Dimethoxy-phenyl)-acetic acid was dissolved in 1,2-dichloroethant (7 mL) and DMF (0.07 nL). Oxalylchloride was added dropwise and the reaction mixture was stirred under argon for 1 h at room temperature. The solvent was removed in vacuo. The crude product was used without further purification.

Preparation of the Compounds of the Invention

1: 2-(3,4-Dimethoxy-phenyl)-N-[5-(2-ethyl-2H-tetrazol-5-yl)-4-phenyl-thiazol-2-yl]-acetamide 200 μL of a 0.6M stock solution of (3,4-dimethoxy-phenyl)-acetic acid was mixed with 200 μL of a 0.3M stock solution of EDC containing 1 eq. of ethyl-diisopropyl-amine. Then 100 μL of a 0.3M stock solution of 5-(2-ethyl-2H-tetrazol-5-yl)-4-phenyl-thiazol-2-ylamine containing 1 eq. of DMAP was added. The reaction mixture was shaken overnight at ambient temperature. Purification was performed by preparative LC-MS. Yield: 13%.

LC/MS (m/z) 452.0 (MH+); RT=2.82; purity (UV, ELSD): 97%; 100%.

The following compounds were prepared analogously:

2: 2-(3,4-Dimethoxy-phenyl)-N-(5-[1,2,4]oxadiazol-3-yl-4-phenyl-thiazol-2-yl)-acetamide LC/MS (m/z) 422.9 (MH+); RT=2.75; purity (UV, ELSD): 98%; 99%.

3: N-(5-Furan-3-yl-4-phenyl-thiazol-2-yl)-isobutyramide

LC/MS (m/z) 313.1 (MH+); RT=3.15; purity (UV, ELSD): 92%; 99%.

4: Cyclopropanecarboxylic acid [5-(2-ethyl-2H-tetrazol-5-yl)-4-phenyl-thiazol-2-yl]-amide LC/MS (m/z) 341.1 (MH+); RT=2.70; purity (UV, ELSD): 98%; 100%.

5: Furan-3-carboxylic acid [5-(2-ethyl-2H-tetrazol-5-yl)-4-phenyl-thiazol-2-yl]-amide LC/MS (m/z) 367.1 (MH+); RT=2.89; purity (UV, ELSD): 72%; 92%.

6: N-[5-(2-Ethyl-2H-tetrazol-5-yl)-4-phenyl-thiazol-2-yl]-isobutyramide

LC/MS (m/z) 343.0 (MH+); RT=2.81; purity (UV, ELSD): 98%; 99%.

7: Furan-2-carboxylic acid [5-(2-ethyl-2H-tetrazol-5-yl)-4-phenyl-thiazol-2-yl]-amide LC/MS (m/z) 367.2 (MH+); RT=2.79; purity (UV, ELSD): 97%; 99%.

8: Cyclohexanecarboxylic acid [5-(2-ethyl-2H-tetrazol-5-yl)-4-phenyl-thiazol-2-yl]-amide LC/MS (m/z) 383.2 (MH+); RT=3.31; purity (UV, ELSD): 93%; 99%.

9: 2-Cyclopentyl-N-[5-(2-ethyl-2H-tetrazol-5-yl)-4-phenyl-thiazol-2-yl]-acetamide LC/MS (m/z) 383.2 (MH+); RT=3.34; purity (UV, ELSD): 99%; 100%.

10: N-[5-(2-Ethyl-2H-tetrazol-5-yl)-4-phenyl-thiazol-2-yl]-propionamide

LC/MS (m/z) 329.1 (MH+); RT=2.63; purity (UV, ELSD): 99%; 100%.

11: Cyclopropanecarboxylic acid (5-[1,2,4]oxadiazol-3-yl-4-phenyl-thiazol-2-yl)-amide LC/MS (m/z) 312.9 (MH+); RT=2.55; purity (UV, ELSD): 95%; 100%.

12: Thiophene-3-carboxylic acid [5-(2-ethyl-2H-tetrazol-5-yl)-4-phenyl-thiazol-2-yl]-amide LC/MS (m/z) 383.1 (MH+); RT=3.03; purity (UV, ELSD): 90%; 99%.

13: 2-Cyclopentyl-N-(5-[1,2,4]oxadiazol-3-yl-4-phenyl-thiazol-2-yl)-acetamide

LC/MS (m/z) 355.1 (MH+); RT=3.18; purity (UV, ELSD): 97%; 99%.

14: Furan-3-carboxylic acid [5-(2-phenethyl-2H-tetrazol-5-yl)-4-phenyl-thiazol-2-yl]-amide LC/MS (m/z) 443.0 (MH+); RT=3.38; purity (UV, ELSD): 70%; 93%.

15: N-(5-Furan-2-yl-4-phenyl-thiazol-2-yl)-isobutyramide

LC/MS (m/z) 313.1 (MH+); RT=3.12; purity (UV, ELSD): 98%; 97%.

16: Furan-2-carboxylic acid (5-furan-3-yl-4-phenyl-thiazol-2-yl)-amide

LC/MS (m/z) 337.0 (MH+); RT=3.14; purity (UV, ELSD): 96%; 99%.

17: 2-(3,4-Dimethoxy-phenyl)-N-(5-furan-2-yl-4-phenyl-thiazol-2-yl)-acetamide

LC/MS (m/z) 421.1 (MH+); RT=3.02; purity (UV, ELSD): 98%; 98%.

18: Cyclopr-opanecarboxylic acid (5-furan-3-yl-4-phenyl-thiazol-2-yl)-amide

100 μL of a 0.3M stock solution of 5-furan-3-yl-4-phenyl-thiazol-2-ylamine and 120 μL of a 0.3M stock solution of pyridine were mixed with 120 μL of a 0.3M stock solution of cyclopropanecarbonyl chloride. The reaction mixture was shaken overnight at ambient temperature. Purification was performed by preparative LC-MS.

Yield: 1.1 mg (12)%.

LC/MS (m/z) 311.1 (MH+); RT=3.11; purity (UV, ELSD): 80%; 97%.

The following compounds were prepared analogously:

19: 2-(3-Methoxy-phenyl)-N-(5-[1,2,4]oxadiazol-3-yl-4-phenyl-thiazol-2-yl)-acetamide LC/MS (m/z) 393.1 (MH+); RT=2.95; purity (UV, ELSD): 96%; 100%.

20: 2-(3-Methoxy-phenyl)-N-[5-(2-phenethyl-2H-tetrazol-5-yl)-4-phenyl-thiazol-2-yl]-acetamide LC/MS (m/z) 497.1 (MH+); RT=3.58; purity (UV, ELSD): 77%; 99%.

21: N-(5-Furan-2-yl-4-phenyl-thiazol-2-yl)-2,2-dimethyl-propionamide

LC/MS (m/z) 327-2 (MH+); RT=3.48; purity (UV, ELSD): 77%; 99%.

22: N-(5-Furan-3-yl-4-phenyl-thiazol-2-yl)-propionamide

LC/MS (m/z) 299.1 (MH+); RT=2.95; purity (UV, ELSD): 96%; 99%.

23: N-[5-(2-Phenethyl-2H-tetrazol-5-yl)-4-phenyl-thiazol-2-yl]-isobutyramide

LC/MS (m/z) 419.3 (MH+); RT=3.33; purity (UV, ELSD): 97%; 99%.

24: N-(5-Furan-2-yl-4-phenyl-thiazol-2-yl)-propionamide

LC/MS (m/z) 299.1 (MH+); RT=2.99; purity (UV, ELSD): 99%; 99%.

25: Furan-2-carboxylic acid [5-(2-methyl-2H-tetrazoI-5-yl)-4-phenyl-thiazol-2-yl]-amide LC/MS (m/z) 353.1 (MH+); RT=2.62; purity (UV, ELSD): 96%; 99%.

26: 3,3-Dimethyl-N-[5-(2-methyl-2H-tetrazol-5-yl)-4-phenyl-thiazol-2-yl]-butyramide LC/MS (m/z) 357.1 (MH+); RT=3.06; purity (UV, ELSD): 98%; 99%.

27: Cyclopropanecarboxylic acid [5-(2-methyl-2H-tetrazol-5-yl)-4-phenyl-thiazol-2-yl]-amide LC/MS (m/z) 327.2 (MH+); RT=2.49; purity (UV, ELSD): 77%; 95%.

28: 2-Cyclopentyl-N-[5-(2-methyl-2H-tetrazol-5-yl)-4-phenyl-thiazol-2-yl]-acetamide LC/MS (m/z) 369.1 (MH+); RT=3.13; purity (UV, ELSD): 94%; 99%.

29: N-[5-(2-Methyl-2H-tetrazol-5-yl)-4-phenyl-thiazol-2-yl]-isobutyramide

LC/MS (m/z) 329.1 (MH+); RT=2.63; purity (UV, ELSD): 96%; 99%.

30: 3-Methyl-N-[5-(2-methyl-2H-tetrazol-5-yl)-4-phenyl-thiazol-2-yl]-butyramide

LC/MS (m/z) 343.1 (MH+); RT=2.86; purity (UV, ELSD): 96%; 99%.

31: N-[5-(2-Methyl-2H-tetrazol-5-yl)-4-phenyl-thiazol-2-yl]-propionamide

LC/MS (m/z) 315.0 (MH+); RT=2.40; purity (UV, ELSD): 90%; 99%.

32: N-[5-(2-Methyl-2H-tetrazol-5-yl)-4-phenyl-thiazol-2-yl]-2-phenyl-acetamide

LC/MS (m/z) 377.1 (MH+); RT=2.85; purity (UV, ELSD): 90%; 99%.

33: Hexanoic acid [5-(2-methlyl-2H-tetrazol-5-yl)-4-phenyl-thiazol-2-yl]-amide

LC/MS (m/z) 357.1 (MH+); RT=3.13; purity (UV, ELSD): 99%; 99%.

34: N-[5-(2-Methyl-2H-tetrazol-5-yl)-4-phenyl-thiazol-2-yl]-2-thiophen-2-yl-acetamide LC/MS (m/z) 383.1 (MH+); RT=2.83; purity (UV, ELSD): 80%; 95%.

35: N-[5-(2-Methyl-2H-tetrazol-5-yl)-4-phenyl-thiazol-2-yl]-acetamide

LC/MS (m/z) 301.0 (MH+); RT=2.13; purity (UV, ELSD): 94%; 99%.

36: 2,2-Dimethyl-N-[5-(2-methyl-2H-tetrazol-5-yl)-4-phenyl-thiazol-2-yl]-propioniamide LC/MS (m/z) 343.1 (MH+); RT=2.92; purity (UV, ELSD): 95%; 99%.

37: Tlhiophene-3-carboxylic acid [5-(2-methyl-2H-tetrazol-5-yl)-4-phenyl-thiazol-2-yl]-amide LC/MS (m/z) 369.1 (MH+); RT=2.85; purity (UV, ELSD): 85%; 99%.

38: N-[4-Phenyl-5-(2-propyl-2H-tetrazol-5-yl)-tlz iazol-2-yl]-isobutyramide

LC/MS (m/z) 357.1 (MH+); RT=3.08; purity (UV, ELSD): 99%; 99%.

39: 3-Methyl-N-[4-phenyl-5-(2-propyl-2H-tetrazol-5-yl)-thiazol-2-yl]-butyramide

LC/MS (m/z) 371.2 (MH+); RT=3.28; purity (UV, ELSD): 97%; 99%.

40: N-[4-Phenyl-5-(2-propyl-2H-tetrazol-5-yl)-tlz iazol-2-yl]-propionamide

LC/MS (m/z) 343.1 (MH+); RT=2.87; purity (UV, ELSD): 90%; 97%.

41: 2-Phenyl-N-[4-phenyl-5-(2-propyl-2H-tetrazol-5-yl)-thiazol-2-yl]-acetamide

LC/MS (m/z) 405.1 (MH+); RT=3.29; purity (UV, ELSD): 94%; 99%.

42: N-[4-Phenyl-5-(2-propyl-2H-tetrazol-5-yl)-tlziazol-2-yl]-2-thiophen-2-yl-acetamide LC/MS (m/z) 411.1 (MH+); RT=3.22; purity (UV, ELSD): 88%; 97%.

43: N-[4-Phenyl-5-(2-propyl-2H-tetrazol-5-yl)-thiazol-2-yl]-acetamide

LC/MS (m/z) 329.1 (MH+); RT=2.65; purity (UV, ELSD): 98%; 99%.

44: 2,2-Ditnethyl-N-[4-phenyl-5-(2-propyl-2H-tetrazol-5-yl)-thiazol-2-yl]-propionamide LC/MS (m/z) 371.2 (MH+); RT=3.34; purity (UV, ELSD): 950/4; 99%.

45: Thiophene-3-carboxylic acid [4-phenyl-5-(2-propyl-2H-tetrazol-5-yl)-thiazol-2-yl]-amide LC/MS (m/z) 397.1 (MH+); RT=3.29; purity (UV, ELSD): 930/4; 99%.

46: N-[5-(2-Butyl-2H-tetrazol-5-yl)-4-phenyl-thiazol-2-yl]-isobutyramide

LC/MS (m/z) 371.2 (MH+); RT=3.31; purity (UV, ELSD): 97%; 99%.

47: 2-Cyclopentyl-N-[5-(2-isobutyl-2H-tetrazol-5-yl)-4-phenyl-thiazol-2-yl]-acetamide LC/MS (m/z) 411.2 (MH+); RT=3.73; purity (UV, ELSD): 98%; 99%.

48: N-[5-(2-Isobutyl-2H-tetrazol-5-yl)-4-phenyl-thiazol-2-yl]-2-thiophen-2-yl-acetamide LC/MS (m/z) 425.1 (MH+); RT=3.40; purity (UV, ELSD): 84%; 95%.

49: N-[5-(2-Cyclopropylmethyl-2H-tetrazol-5-yl)-4-phenyl-thiazol-2-yl]-3-methyl-butyramide LC/MS (m/z) 383.2 (MH+); RT=3.32; purity (UV, ELSD): 86%; 98%.

50: Furan-2-carboxylic acid [5-(3-methyl-[1,2,4]oxadiazol-5-yl)-4-phenyl-thiazol-2-yl]-amide Prepared from 5-(3-methyl-[1,2,4]oxadiazol-5-yl)-4-phenyl-thiazol-2-ylamine and furan-2-carbonyl chloride.

LC/MS (m/z) 353.4 (MH+); RT=2.84

51: 3,3-Dimethyl-N-[5-(5-methyl-[1,2,4]oxadiazol-3-yl)-4-phenyl-thiazol-2-yl]-butyramide Prepared from 5-(5-methyl-[1,2,4]oxadiazol-3-yl)-4-phenyl-thiazol-2-ylamine and 3,3-dimethyl-butyryl chloride.

LC/MS (m/z) 357.4 (MH+); RT=3.21

52: N-[5-(3-Methyl-[1,2,4]oxadiazol-5-yl)-4-phenyl-thiazol-2-yl]-benzamide

Prepared from 5-(3-methyl-[1,2,4]oxadiazol-5-yl)-4-phenyl-thiazol-2-ylamine and benzoyl chloride.

LC/MS (m/z) 363.4 (MH+); RT=3.22

53: N-[5-(3-Ethyl-[1,2,4]oxadiazol-5-yl)-4-phenyl-tziazol-2-yl]-benzamide

Prepared from 5-(3-Ethyl-[1,2,4]oxadiazol-5-yl)-4-phenyl-thiazol-2-ylamine and benzoyl chloride.

LC/MS (m/z) 377.4 (MH+); RT=3.48

54: N-[5-(5-Methyl-[1,2,4]oxadiazol-3-yl)-4-phenyl-thiazol-2-yl]-benzamide

Prepared from 5-(5-methyl-[1,2,4]oxadiazol-3-yl)-4-phenyl-thiazol-2-ylamine and benzoyl chloride.

LC/MS (m/z) 363.4 (MH+); RT=3.11

55: Cyclopropanecarboxylic acid [5-(3-methyl-[1,2,4]oxadiazol-5-yl)-4-phenyl-thiazol-2-yl]-amide Prepared from 5-(3-methyl-[1,2,4]oxadiazol-5-yl)-4-phenyl-thiazol-2-ylamine and cyclopropanecarbonyl chloride.

LC/MS (m/z) 327.4 (MH+); RT=2.74

56: Cyclopropanecarboxylic acid [5-(3-ethyl-[1,2,4]oxadiazol-5-yl)-4-phenyl-thiazol-2-yl]-amide Prepared from 5-(3-Ethyl-[1,2,4]oxadiazol-5-yl)-4-phenyl-thiazol-2-ylamine and cyclopropanecarbonyl chloride.

LC/MS (m/z) 341.4 (MH+); RT=3.05

57: Cyclopropanecarboxylic acid [5-(5-methyl-[1,2,4]oxadiazol-3-yl)-4-phenyl-thiazol-2-yl]-amide Prepared from 5-(5-methyl-[1,2,4]oxadiazol-3-yl)-4-phenyl-thiazol-2-ylamine and cyclopropanecarbonyl chloride.

LC/MS (m/z) 327.4 (MH+); RT=2.62

58: Cyclopropanecarboxylic acid [5-(5-ethyl-[1,2,4]oxadiazol-3-yl)-4-phenyl-thiazol-2-yl]-amide Prepared from 5-Ethyl-3-(4-phenyl-thiazol-5-yl)-[1,2,4]oxadiazole and cyclopropanecarbonyl chloride.

LC/MS (m/z) 341.4 (MH+); RT=2.96

59: 2-Cyclopentyl-N-[5-(3-methyl-[1,2,4]oxadiazol-5-yl)-4-phenyl-tlbiazol-2-yl]-acetamide Prepared from 5-(3-methyl-[1,2,4]oxadiazol-5-yl)-4-phenyl-thiazol-2-ylamine and cyclopentyl-acetyl chloride.

LC/MS (m/z) 369.5 (MH+); RT=3.43

60: 2-Cyclopentyl-N-[5-(3-ethyl-[1,2,4]oxadiazol-5-yl)-4-phenyl-thiazol-2-yl]-acetamide Prepared from 5-(3-ethyl-[1,2,4]oxadiazol-5-yl)-4-phenyl-thiazol-2-ylamine and cyclopentyl-acetyl chloride.

LC/MS (m/z) 383.5 (MH+); RT=3.68

61: 2-Cyclopentyl-N-[5-(5-methyl-[1,2,4]oxadiazol-3-yl)-4-phenyl-thiazol-2-yl]-acetamide Prepared from 5-(5-methyl-[1,2,4]oxadiazol-3-yl)-4-phenyl-thiazol-2-ylamine and cyclopentyl-acetyl chloride.

LC/MS (m/z) 369.5 (MH+); RT=3.30

62: 2-Cyclopentyl-N-[5-(5-ethyl-[1,2,4]oxadiazol-3-yl)-4-phenyl-thiazol-2-yl]-acetamide Prepared from 5-ethyl-3-(4-phenyl-thiazol-5-yl)-[1,2,4]oxadiazole and cyclopentyl-acetyl chloride.

LC/MS (m/z) 383.5 (MH+); RT=3.57

63: Cyclohexanecarboxylic acid [5-(3-methyl-[1,2,4]oxadiazol-5-yl)-4-phenyl-thiazol-2-yl]-amide Prepared from 5-(3-methyl-[1,2,4]oxadiazol-5-yl)-4-phenyl-thiazol-2-ylamine and cyclohexanecarbonyl chloride.

LC/MS (m/z) 369.5 (MH+); RT=3.41

64: Cyclohexanecarboxylic acid [5-(3-ethyl-[1,2,4]oxadiazol-5-yl)-4-phenyl-thiazol-2-yl]-amide Prepared from 5-(3-ethyl-[1,2,4]oxadiazol-5-yl)-4-phenyl-thiazol-2-ylamine and cyclohexanecarbonyl chloride.

LC/MS (m/z) 383.5 (MH+); RT=3.67

65: Cyclohexanecarboxylic acid [5-(5-methyl-[1,2,4]oxadiazol-3-yl)-4-phenyl-thiazol-2-yl]-amide Prepared from 5-(5-methyl-[1,2,4]oxadiazol-3-yl)-4-phenyl-thiazol-2-ylamine and cyclohexanecarbonyl chloride.

LC/MS (m/z) 369.5 (MH+); RT=3.29

66: N-[5-(1-Methyl-1H-tetrazol-5-yl)-4-phenyl-thiazol-2-yl]-isobutyramide

Prepared from 5-(1-methyl-1H-tetrazol-5-yl)-4-phenyl-thiazol-2-ylamine and isobutyryl chloride.

LC/MS (m/z) 329.4 (MH+); RT=2.48

67: N-[5-(3-Ethyl-[1,2,4]oxadiazol-5-yl)-4-phenyl-thiazol-2-yl]-isobutyramide

Prepared from 5-(3-ethyl-[1,2,4]oxadiazol-5-yl)-4-phenyl-thiazol-2-ylamine and isobutyryl chloride.

LC/MS (m/z) 343.4 (MH+); RT=3.17

68: 3-Methfyl-N-[5-(3-methyl-[1,2,4]oxadiazol-5-yl)-4-phenyl-thiazol-2-yl]-butyramide Prepared from 5-(3-methyl-[1,2,4]oxadiazol-5-yl)-4-phenyl-thiazol-2-ylamine and 3-methyl-butyryl chloride.

LC/MS (m/z) 343.4 (MH+); RT=3.13

69: N-[5-(3-Ethyl-[1,2,4]oxadiazol-5-yl)-4-phenyl-thiazol-2-yl]-3-methyl-butyramide Prepared from 5-(3-ethyl-[1,2,4]oxadiazol-5-yl)-4-phenyl-thiazol-2-ylamine and 3-methyl-butyryl chloride.

LC/MS (m/z) 357.4 (MH+); RT=3.40

70: 3-Methyl-N-[5-(5-methyl-[1,2,4]oxadiazol-3-yl)-4-phenyl-thiazol-2-yl]-butyramide Prepared from 5-(5-methyl-[1,2,4]oxadiazol-3-yl)-4-phenyl-thiazol-2-ylamine and 3-methyl-butyryl chloride.

LC/MS (m/z) 343.4 (MH+); RT=3.00

71: N-[5-(3-Methyl-[1,2,4]oxadiazol-5-yl)-4-phenyl-thiazol-2-yl]-propionamide

Prepared from 5-(3-methyl-[1,2,4]oxadiazol-5-yl)-4-phenyl-thiazol-2-ylamine and propionyl chloride.

LC/MS (m/z) 315.4 (MH+); RT=2.63

72: N-[5-(3-Ethyl-[1,2,4]oxadiazol-5-yl)-4-phenyl-thiazol-2-yl]-propionamide

Prepared from 5-(3-ethyl-[1,2,4]oxadiazol-5-yl)-4-phenyl-thiazol-2-ylamine and propionyl chloride.

LC/MS (m/z) 329.4 (MH+); RT=2.94

73: N-[5-(5-Methyl-[1,2,4]oxadiazol-3-yl)-4-phenyl-thiazol-2-yl]-propionamide

Prepared from 5-(5-methyl-[1,2,4]oxadiazol-3-yl)-4-phenyl-thiazol-2-ylamine and propionyl chloride.

LC/MS (m/z) 315.4 (MH+); RT=2.52

74: N-[5-(3-Methyl-[1,2,4]oxadiazol-5-yl)-4-phenyl-thiazol-2-yl]-2-phenyl-acetamide Prepared from 5-(3-methyl-[1,2,4]oxadiazol-5-yl)-4-phenyl-thiazol-2-ylamine and phenyl-acetyl chloride.

LC/MS (m/z) 377.4 (MH+); RT=3.15

75: N-[5-(3-Ethyl-[1,2,4]oxadiazol-5-yl)-4-phenyl-thiazol-2-yl]-2-phenyl-acetamide Prepared from 5-(3-ethyl-[1,2,4]oxadiazol-5-yl)-4-phenyl-thiazol-2-ylamine and phenyl-acetyl chloride.

LC/MS (m/z) 391.5 (MH+); RT=3.39

76: N-[5-(5-Methyl-[1,2,4]oxadiazol-3-yl)-4-phenyl-thiazol-2-yl]-2-phenyl-acetamide Prepared from 5-(5-methyl-[1,2,4]oxadiazol-3-yl)-4-phenyl-thiazol-2-ylamine and phenyl-acetyl chloride.

LC/MS (m/z) 377.4 (MH+); RT=3.04

77: N-[5-(5-Oxo-4,5-dihydro-[1,3,4]oxadiazol-2-yl)-4-phenyl-thiazol-2-yl]-2-phenyl-acetamide Prepared from 5-(2-amino-4-phenyl-thiazol-5-yl)-3H-[1,3,4]oxadiazol-2-one and phenyl-acetyl chloride.

LC/MS (m/z) 379.4 (MH+); RT=2.59

78: N-[5-(5-Ethyl-[1,2,4]oxadiazol-3-yl)-4-phenyl-thiazol-2-yl]-3-phenyl-acrylamide Prepared from 5-ethyl-3-(4-phenyl-thiazol-5-yl)-[1,2,4]oxadiazole and 3-phenyl-acryloyl chloride.

LC/MS (m/z) 403.5 (MH+); RT=3.54

79: Hexanoic acid [5-(3-methyl-[1,2,4]oxadiazol-5-yl)-4-phenyl-thiazol-2-yl]-amide Prepared from 5-(3-methyl-[1,2,4]oxadiazol-5-yl)-4-phenyl-thiazol-2-ylamine and hexanoyl chloride.

LC/MS (m/z) 357.4 (MH+); RT=3.41

80: Hexanoic acid [5-(5-methyl-[1,2,4]oxadiazol-3-yl)-4-phenyl-thiazol-2-yl]-amide Prepared from 5-(5-methyl-[1,2,4]oxadiazol-3-yl)-4-phenyl-thiazol-2-ylamine and hexanoyl chloride.

LC/IMS (m/z) 357.4 (MH+); RT=3.29

81: N-[5-(3-Methyl-[1,2,4]oxadiazol-5-yl)-4-phenyl-thiazol-2-yl]-2-thiophen-2-yl-acetamide Prepared from 5-(3-methyl-[1,2,4]oxadiazol-5-yl)-4-phenyl-thiazol-2-ylamine and thiophen-2-yl-acetyl chloride.

LC/MS (m/z) 383.5 (MH+); RT=3.06

82: N-[5-(3-Ethyl-[1,2,4]oxadiazol-5-yl)-4-phenyl-thiazol-2-yl]-2-thiophen-2-yl-acetamide Prepared from 5-(3-ethyl-[1,2,4]oxadiazol-5-yl)-4-phenyl-thiazol-2-ylamine and thiophen-2-yl-acetyl chloride.

LC/MS (m/z) 397.5 (MH+); RT=3.31

83: N-[5-(5-Methyl-[1,2,4]oxadiazol-3-yl)-4-phenyl-thiazol-2-yl]-2-thiophen-2-yl-acetamide Prepared from 5-(5-methyl-[1,2,4]oxadiazol-3-yl)-4-phenyl-thiazol-2-ylamine and thiophen-2-yl-acetyl chloride.

LC/MS (m/z) 383.5 (MH+); RT=2.97

84: N-[5-(3-Methyl-[1,2,4]oxadiazol-5-yl)-4-phenyl-thiazol-2-yl]-acetamide

Prepared from 5-(3-methyl-[1,2,4]oxadiazol-5-yl)-4-phenyl-thiazol-2-ylamine and acetyl chloride.

LC/MS (m/z) 301.3 (MH+); RT=2.38

85: N-[5-(3-Ethyl-[1,2,4]oxadiazol-5-yl)-4-phenyl-thiazol-2-yl]-acetamide

Prepared from 5-(3-ethyl-[1,2,4]oxadiazol-5-yl)-4-phenyl-thiazol-2-ylamine and acetyl chloride.

LC/MS (m/z) 315.4 (MH+); RT=2.65

86: N-[5-(5-Methyl-[1,2,4]oxadiazol-3-yl)-4-phenyl-thiazol-2-yl]-acetamide

Prepared from 5-(5-methyl-[1,2,4]oxadiazol-3-yl)-4-phenyl-thiazol-2-ylamine and acetyl chloride.

LC/MS (m/z) 301.3 (MH+); RT=2.28

87: 2,2-Dimethyl-N-[5-(3-methyl-[, 2,4]oxadiazol-5-yl)-4-phenyl-thiazol-2-yl]-propionamide Prepared from 5-(3-methyl-[1,2,4]oxadiazol-5-yl)-4-phenyl-thiazol-2-ylamine and 2,2-dimethyl-propionyl chloride.

LC/MS (m/z) 343.4 (MH+); RT=3.27

88: N-[5-(3-Ethyl-[, 2,4]oxadiazol-5-yl)-4-phenyl-thiazol-2-yl]-2,2-dimethyl-propionamide Prepared from 5-(3-ethyl-[1,2,4]oxadiazol-5-yl)-4-phenyl-thiazol-2-ylamine and 2,2-dimethyl-propionyl chloride.

LC/MS (m/z) 357.4 (MH+); RT=3.46

89: 2,2-Dimethyl-N-[5-(5-methyl-[1,2,4]oxadiazol-3-yl)-4-phenyl-thiazol-2-yl]-propionamide Prepared from 5-(5-methyl-[1,2,4]oxadiazol-3-yl)-4-phenyl-thiazol-2-ylamine and 2,2-dimethyl-propionyl chloride.

LC/MS (m/z) 343.4 (MH+); RT=3.07

90: Furan-3-carboxylic acid [5-(2-methyl-2H-tetrazol-5-yl)-4-(4H-1lambda*4*-thiophen-2-yl)-thiazol-2-yl]-amide Prepared from 5-(2-methyl-2H-tetrazol-5-yl)-4-thiophen-2-yl-thiazol-2-ylamine and furan-3-carbonyl chloride.

LC/MS (m/z) 361.4 (MH+); RT=2.75

91: Thiophene-3-carboxylic acid [5-(3-methyl-[1,2,4]oxadiazol-5-yl)-4-phenyl-thiazol-2-yl]-amide Prepared from 5-(3-methyl-[1,2,4]oxadiazol-5-yl)-4-phenyl-thiazol-2-ylamine and thiophene-3-carbonyl chloride.

LC/MS (m/z) 369.4 (MH+); RT=3.18

92: Thiophene-3-carboxylic acid [5-(5-methyl-[1,2,4]oxadiazol-3-yl)-4-phenyl-thiazol-2-yl]-amide Prepared from 5-(5-methyl-[1,2,4]oxadiazol-3-yl)-4-phenyl-thiazol-2-ylamine and thiophene-3-carbonyl chloride.

LC/MS (m/z) 369.4 (MH+); RT=3.01

93: 2-(3,4-Dimethoxy-phenyl)-N-[5-(2-methyl-2H-tetrazol-yl)-4-thiophen-2-yl-thiazol-2-yl]-acetamide Prepared from 5-(2-methyl-2H-tetrazol-5-yl)-4-thiophen-2-yl-thiazol-2-ylamine and (3,4-dimethoxy-phenyl)-acetyl chloride.

LC/MS (m/z) 445.5 (MH+); RT=2.69

| No. | Structure |
| --- | --- |
| 1 | 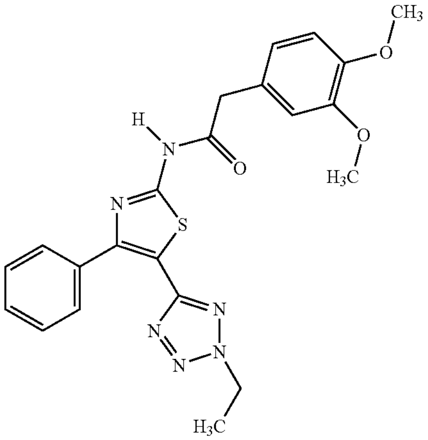 |
| 2 | 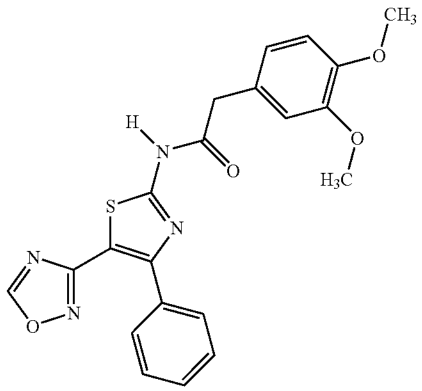 |
| 3 | 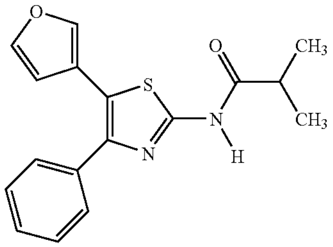 |
| 4 | 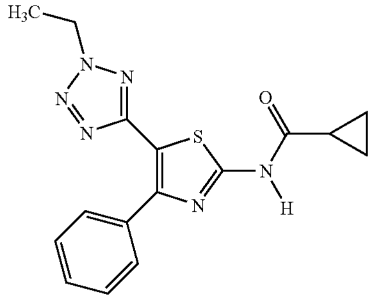 |
-continued
| No. | Structure |
| --- | --- |
| 5 | 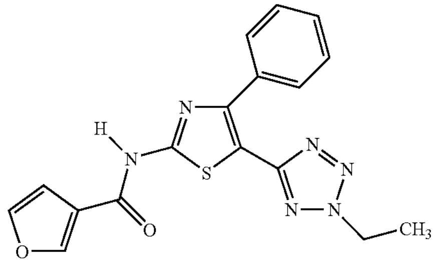 |
| 6 | 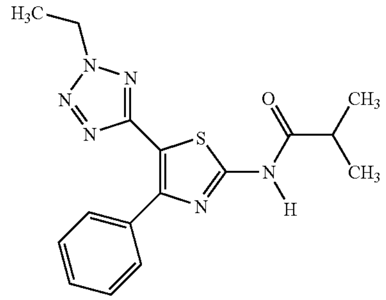 |
| 7 | 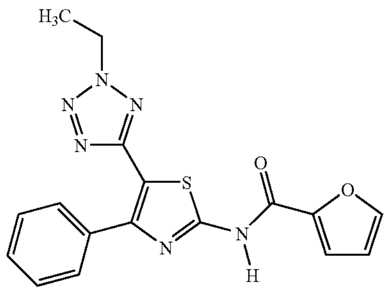 |
| 8 | 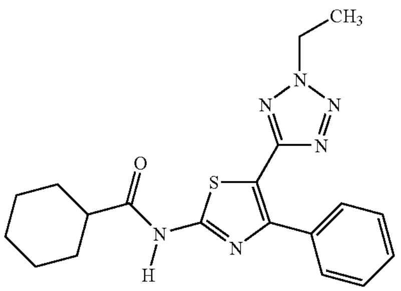 |
| 9 | 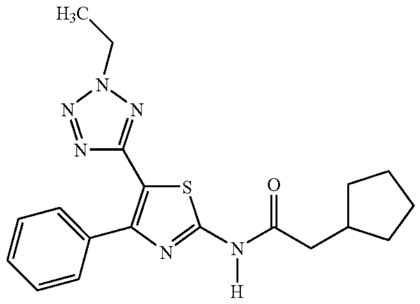 |

-continued
| No. | Structure |
|---|---|
| 10 | 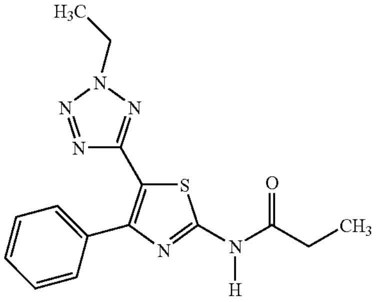 |
| 11 | 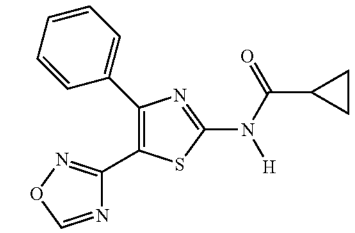 |
| 12 | 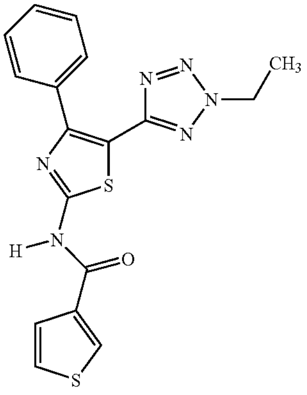 |
| 13 | 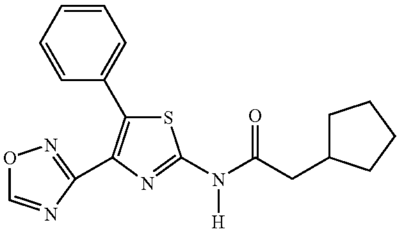 |
| 14 | 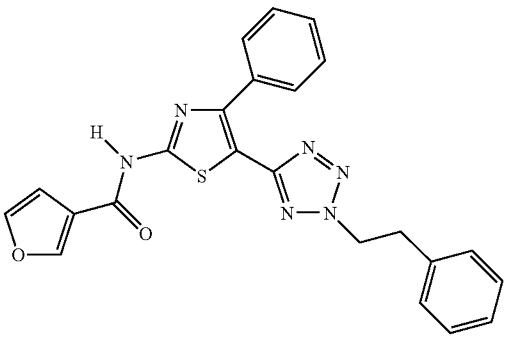 |
-continued
| No. | Structure |
|---|---|
| 15 | 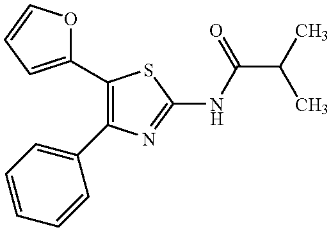 |
| 16 | 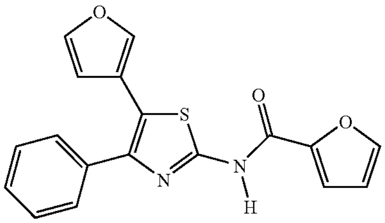 |
| 17 | 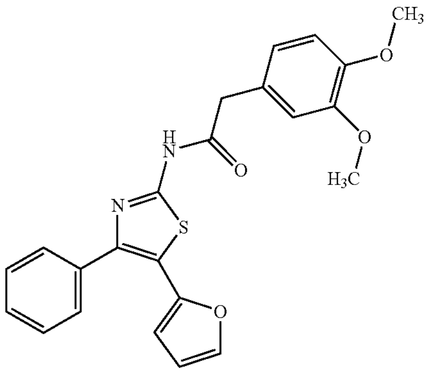 |
| 18 | 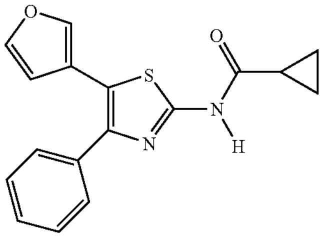 |
| 19 | 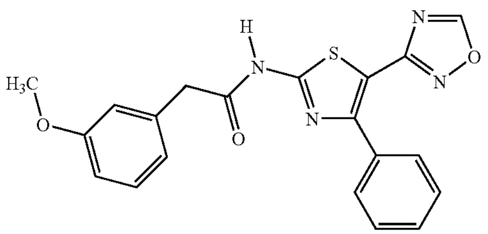 |

-continued
| No. | Structure |
| --- | --- |
| 20 | 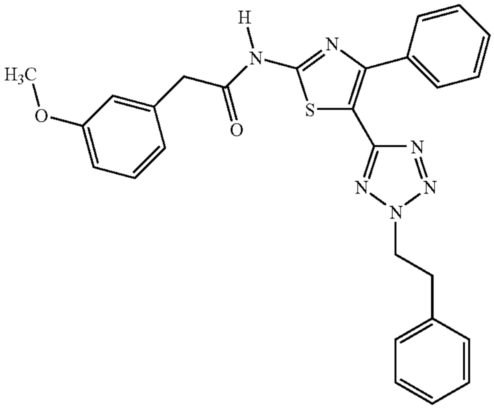 |
| 21 | 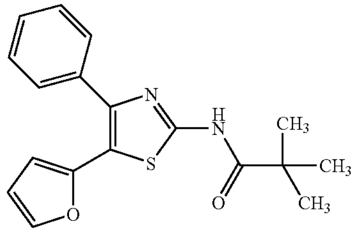 |
| 22 | 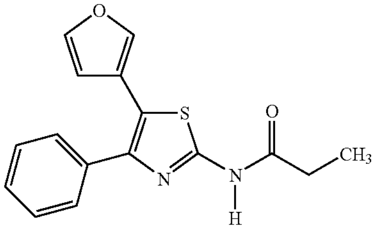 |
| 23 | 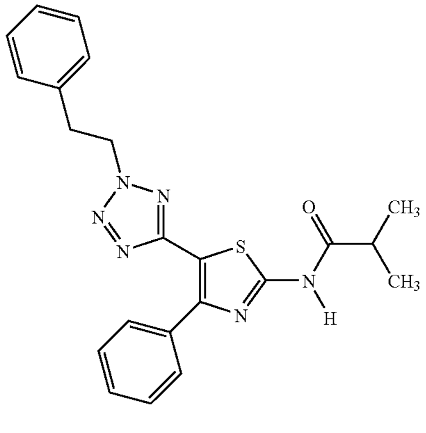 |
| 24 | 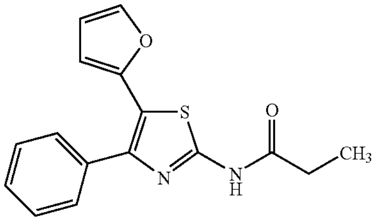 |
-continued
| No. | Structure |
| --- | --- |
| 25 | 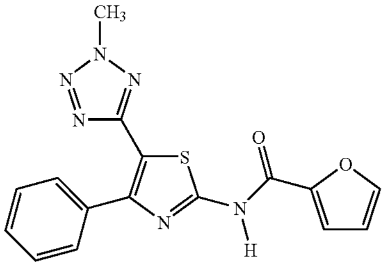 |
| 26 | 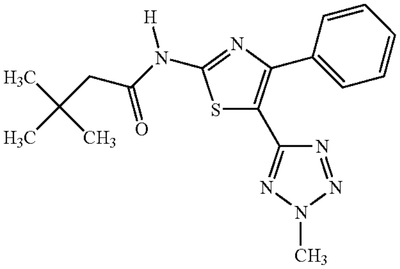 |
| 27 | 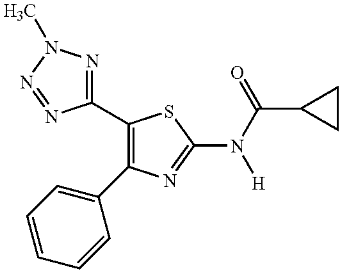 |
| 28 | 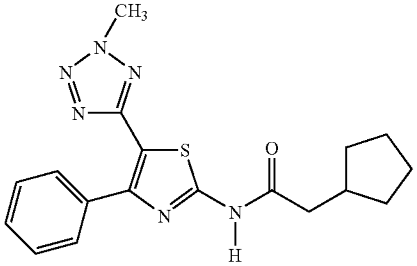 |
| 29 | 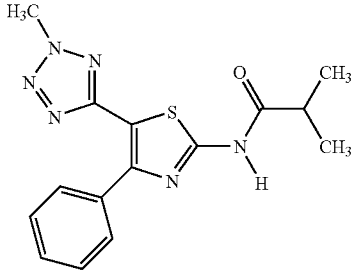 |

-continued
| No. | Structure |
|---|---|
| 30 | 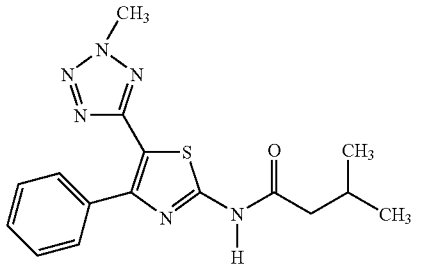 |
| 31 | 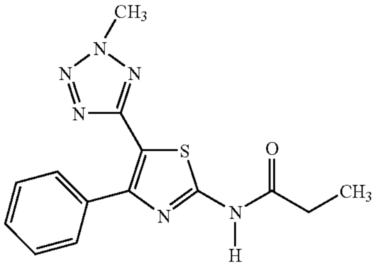 |
| 32 | 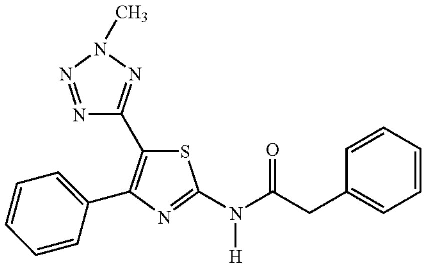 |
| 33 | 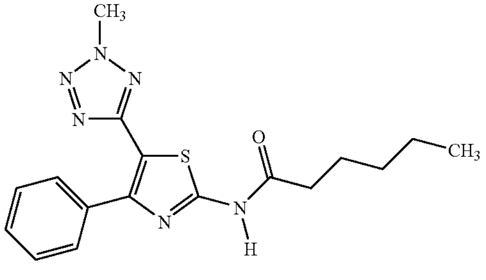 |
| 34 | 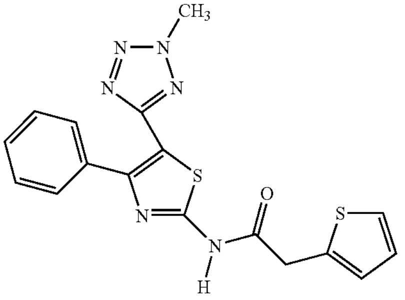 |
-continued
| No. | Structure |
|---|---|
| 35 | 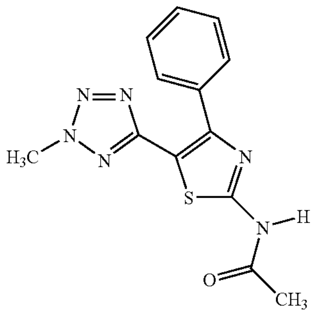 |
| 36 | 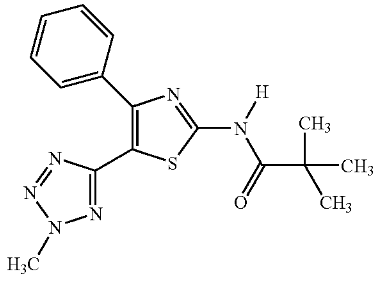 |
| 37 | 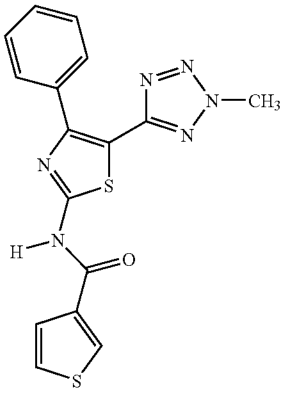 |
| 38 | 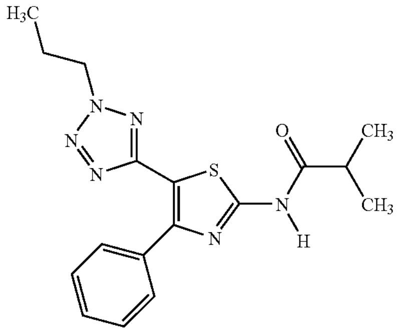 |

-continued
| No. | Structure |
| --- | --- |
| 39 | 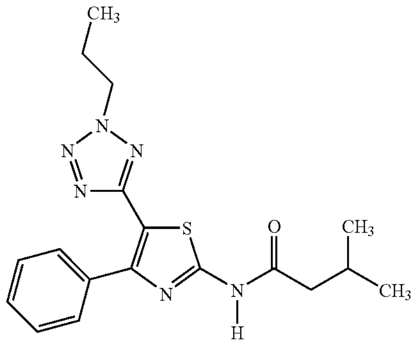 |
| 40 | 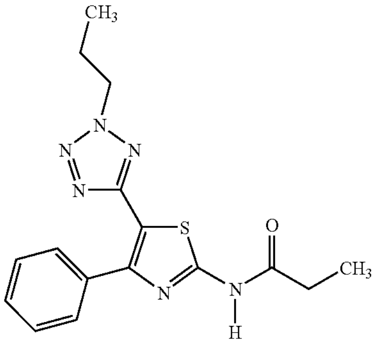 |
| 41 | 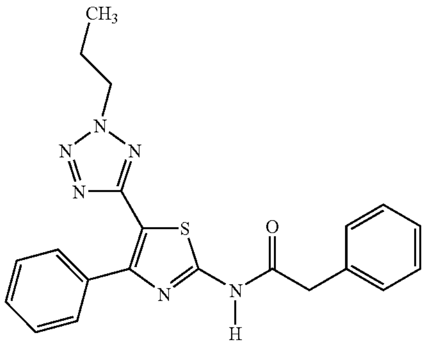 |
| 42 | 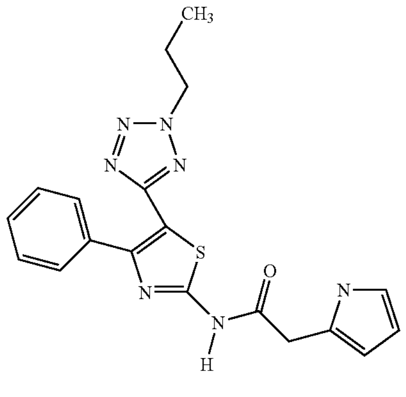 |
-continued
| No. | Structure |
| --- | --- |
| 43 | 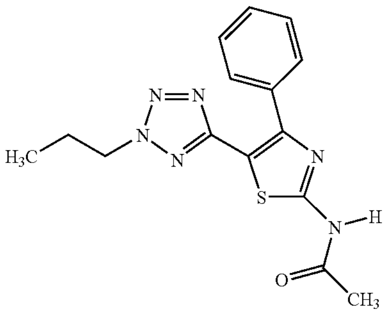 |
| 44 | 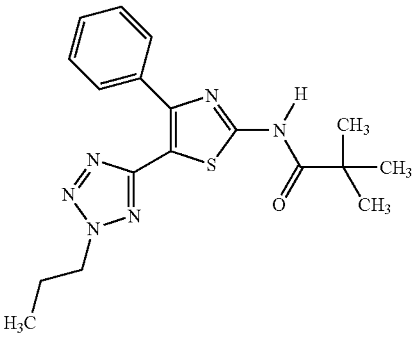 |
| 45 | 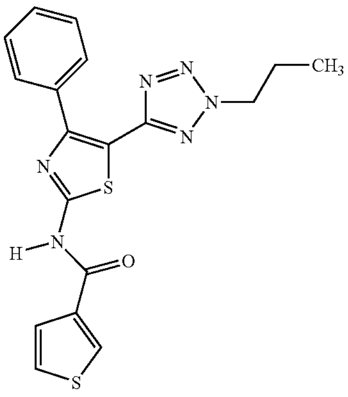 |
| 46 | 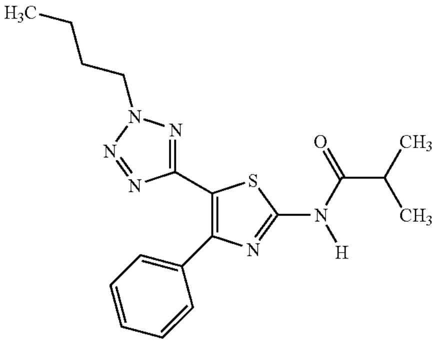 |

-continued
| No. | Structure |
| --- | --- |
| 47 | 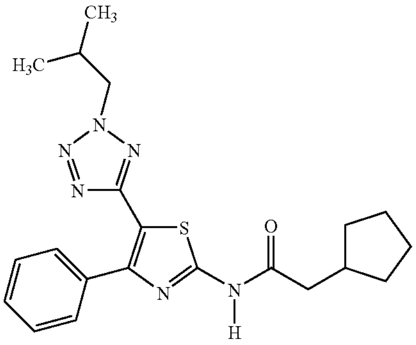 |
| 48 | 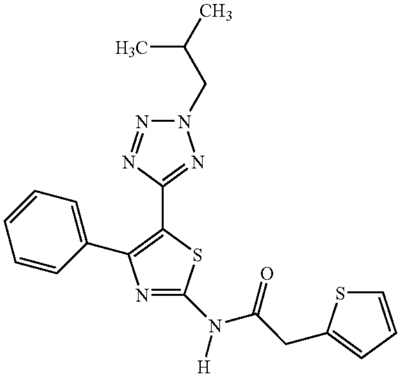 |
| 49 | 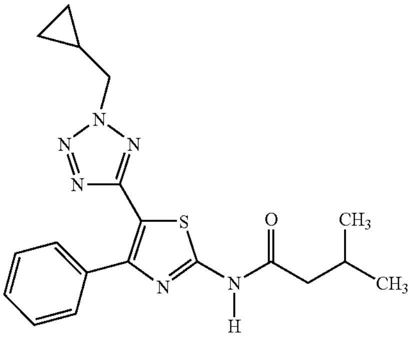 |
| 50 | 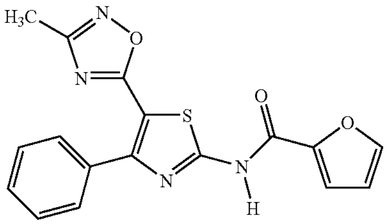 |
| 51 | 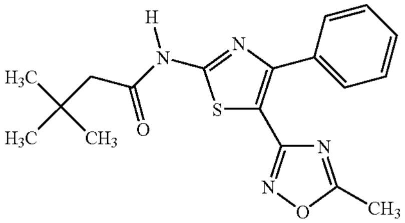 |
-continued
| No. | Structure |
| --- | --- |
| 52 | 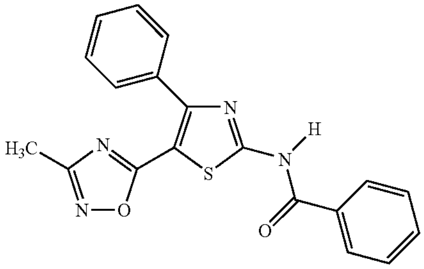 |
| 53 | 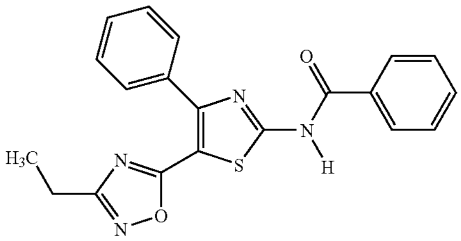 |
| 54 | 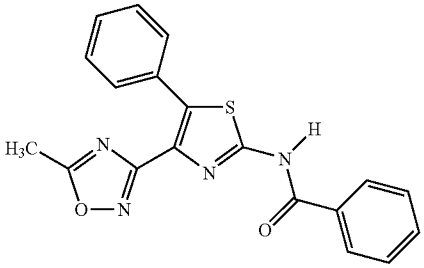 |
| 55 | 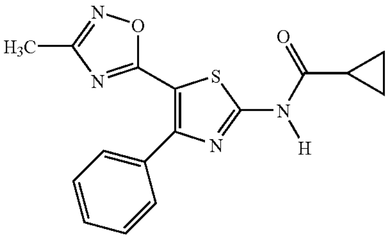 |
| 56 | 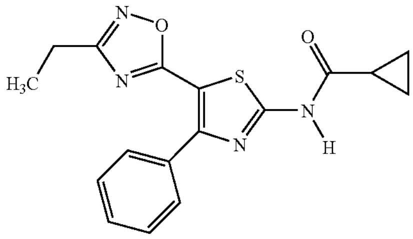 |
| 57 | 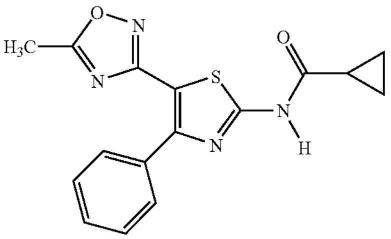 |

-continued
| No. | Structure |
| --- | --- |
| 58 | 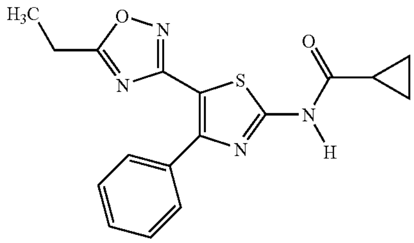 |
| 59 | 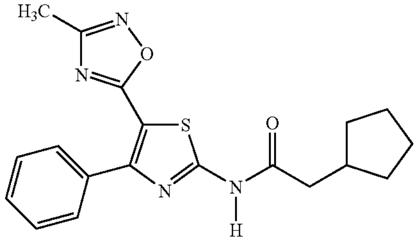 |
| 60 | 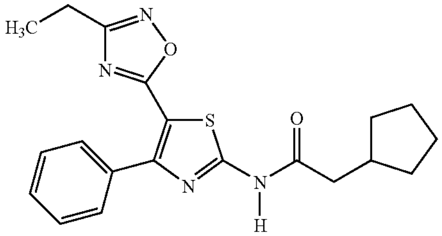 |
| 61 | 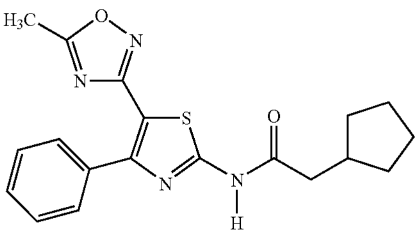 |
| 62 | 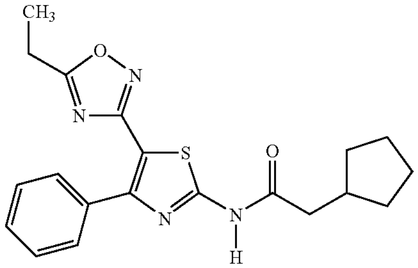 |
| 63 | 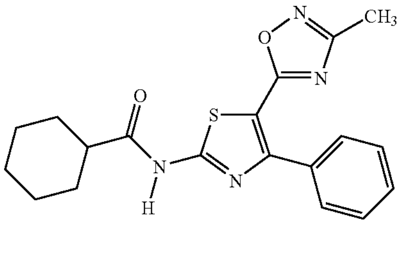 |
-continued
| No. | Structure |
| --- | --- |
| 64 | 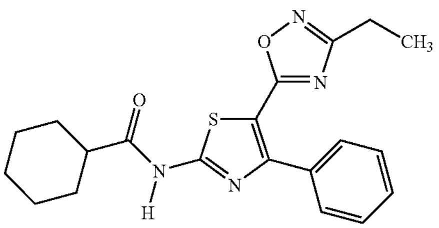 |
| 65 | 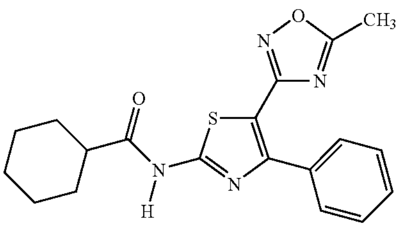 |
| 66 | 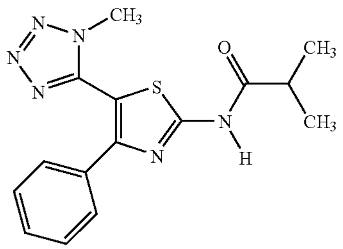 |
| 67 | 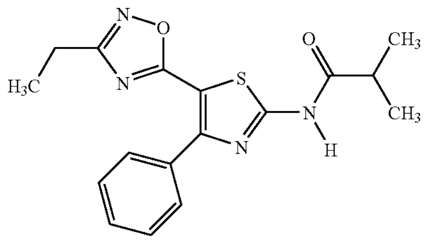 |
| 68 | 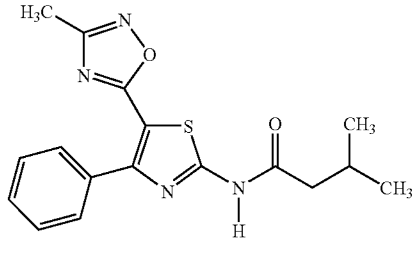 |
| 69 | 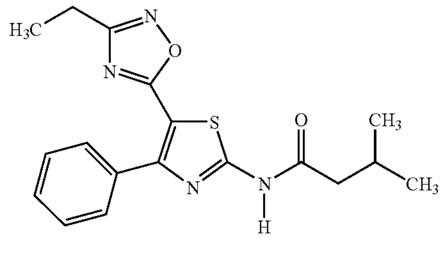 |

-continued
| No. | Structure |
| --- | --- |
| 70 | 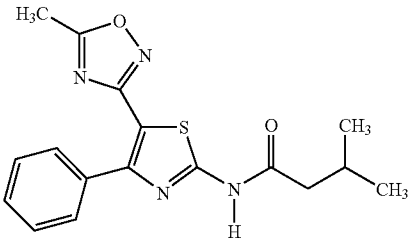 |
| 71 | 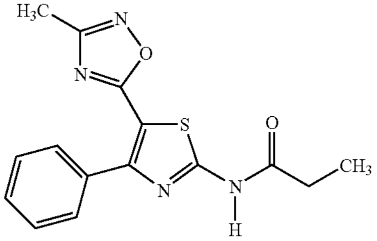 |
| 72 | 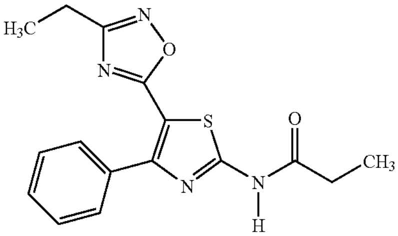 |
| 73 | 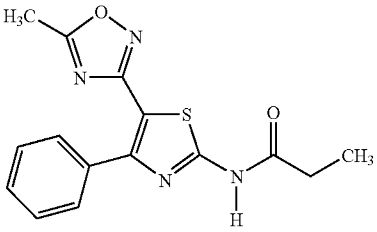 |
| 74 | 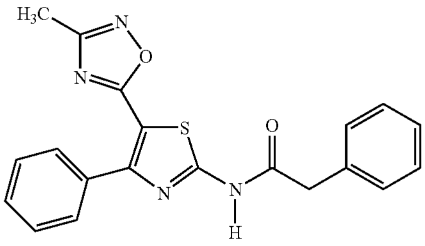 |
| 75 | 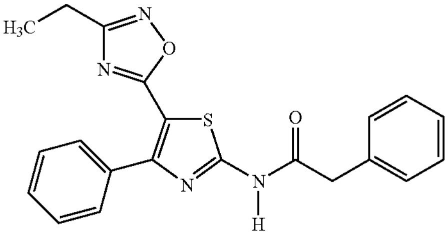 |
-continued
| No. | Structure |
| --- | --- |
| 76 | 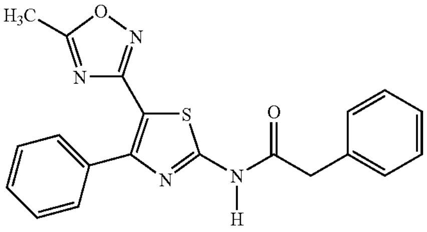 |
| 77 | 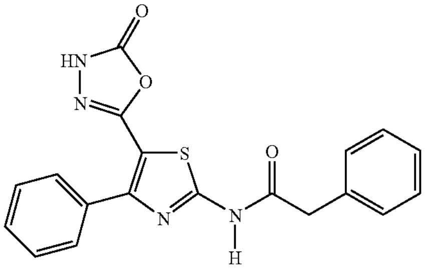 |
| 78 | 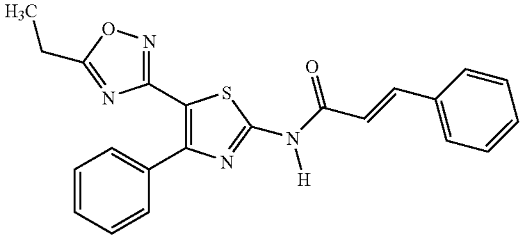 |
| 79 | 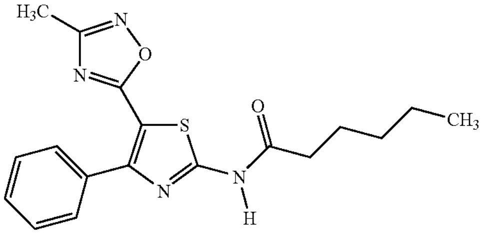 |
| 80 | 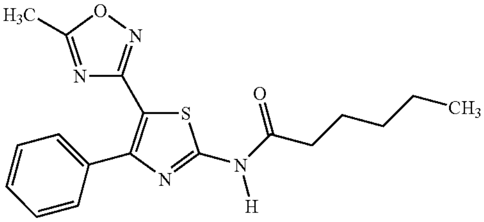 |
| 81 | 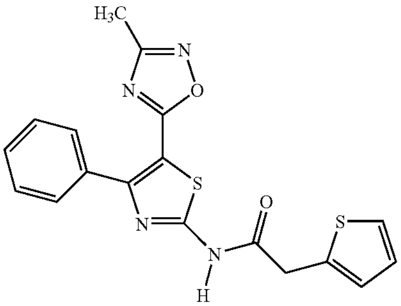 |

-continued
| No. | Structure |
| --- | --- |
| 82 | 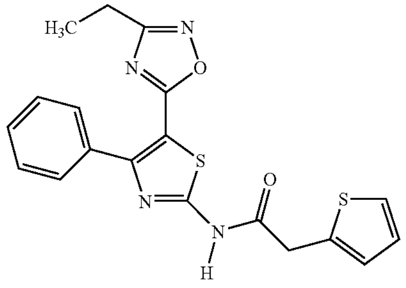 |
| 83 | 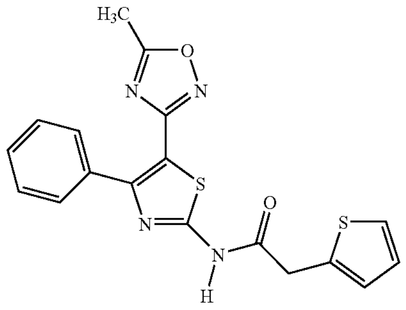 |
| 84 | 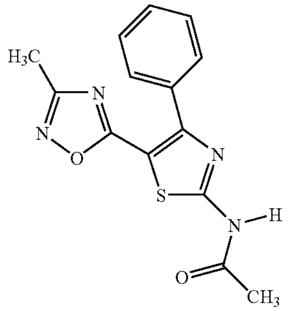 |
| 85 | 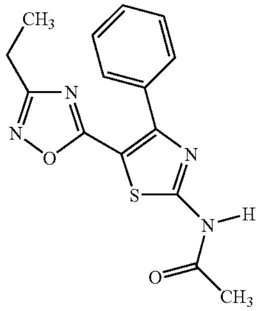 |
| 86 | 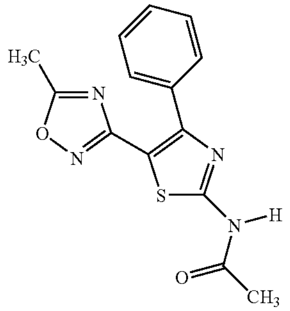 |
-continued
| No. | Structure |
| --- | --- |
| 87 | 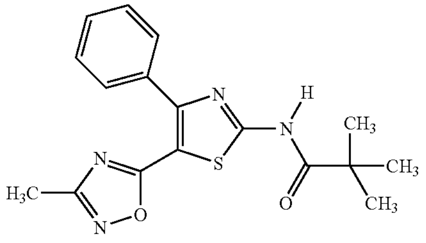 |
| 88 | 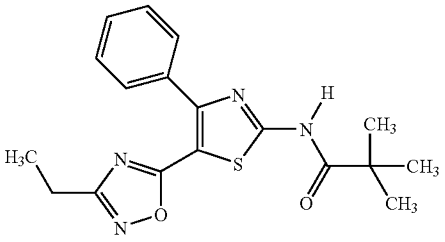 |
| 89 | 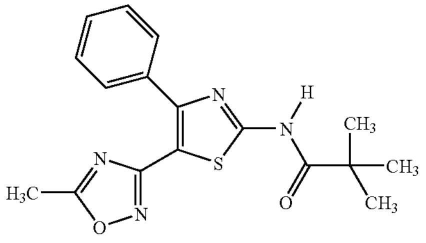 |
| 90 | 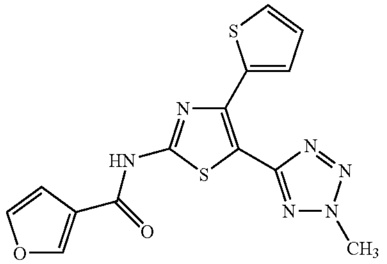 |
| 91 | 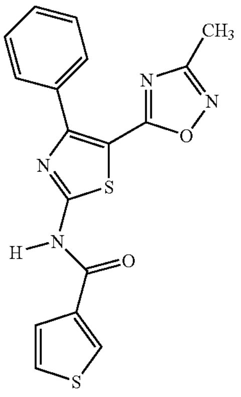 |

-continued

| No. | Structure |
|---|---|
| 92 | 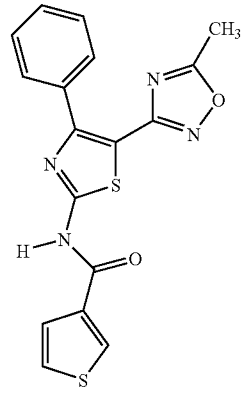 |
| 93 | 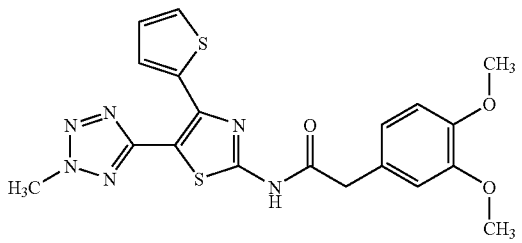 |

Pharmacological Testing

The compounds of the invention were tested according to the following methods:

$A_{2A}$ Efficacy Assays

Cloning of the human cDNA encoding the $A_{2a}$ receptor. cDNA was obtained by random primed reverse transcription of human fetal brain RNA (Clonetech). A subsequent polymerase chain reaction (PCR) was performed using the cDNA as template and the oligonucleotides TTTACGCGTGGCCATGCCCATCATGGGCTCCTC (SEQ ID NO:1) and TTTCTAGAATCAGGACACTCCTGCTCCATC (SEQ ID NO:2) as primers for the amplification. The amplification was performed using Pfu polymerase (Stratagene, in accordance with the manufactures recommendation) with an annealing temperature of 54° C. The reaction mixture was analyzed by an agarose gel electrophoresis and a band of 1.2 kb was excised and the DNA eluded. The eluded DNA was digested with the restriction enzymes MluI and XbaI and ligated into a vector, pClneo, cut with the same enzymes. DNA was isolated and sequenced. CHO cells was transfected with the pClneo clone expressing the $A_{2a}$ receptor and cells with stable integration of the plasmids were isolated after 2-3 weeks growth in the presence of either 5 mg/ml or 10mg/ml G418.

CHO cells transfected with $A_{2A}$ receptors as described above were grown in F12 nutrient mixture (kaighs modification, Life technologies) with 10% FCS, 1% glutamin and 1% penicillin/streptomycin and 1 mg/mL G418.

24 h prior to assay performance, 10000 cells/well were seeded in costar 96-well plates in media without G418 to 60-80% confluence. The cells were stimulated with NECA (00-9498, final concentration 75 nM) corresponding to about 80% agonist efficacy.

The cell media was removed and the cells washed 3 times in 37° C. pre-equilibrated PBS and incubated (on shaker) with 10 μL of a suspension of acceptor beads and 10 μL of a solution of test compound or standard compound (0-10 μM) in darkness for 30 min at 25° C. before addition of 30 μl of a suspension of donor beads and further incubation 60-120 min in darkness. The plates were analysed according to manufacturers instruction (Alpha screen, Perkin Elmer (Pachard Biosciense)).

The acceptor beads were suspended in a stimulation buffer (5 mM HEPES, 0.1% BSA in Hanks balanced salt pH 7.4 w/o phenol red (Gibco). The donor beads were suspended in a lysis buffer (the stimulation buffer with 0.3% Tween 20 and biotinylated cAMP) according to manufacturers instruction (Alpha screen, Perkin Elmer (Pachard Biosciense)).

The data were fitted with non-linear regression, and $IC_{50}$ and $K_i$ values were calculated from the equations:

$$IC_{50}=([I]/(100/(100-\%\,INH))/(1+([ag]/EC_{50})$$

and $$K_i=IC_{50}/(1-[ag]/EC_{50}),$$

where [I] is the inhibitor concentration, [ag] is the assay agonist concentration and $EC_{50}$ is the agonist concentration required for half maximal effect.

$A_{2A}$ Binding Assay:

Membrane preparations for $A_{2A}$ Binding Analysis: Expression in Insect Cells

The human $A_{2a}$ encoding DNA were excised from the pClneo constructs by MluI and XbaI and subcloned into the pFASTBAC2 vector cut with XbaI and BssHII. The inserts were recombined into the baculo vector using the Bac-to-Bac® system (Invitrogen). The generation and isolation of baculo virus was performed as described by the distributor (Invitrogen). High Five cells (Invitrogen) was grown at 27° C. in suspension to a density of $1*10^6$ and infected with a MOI of 0.5. The cells are harvested 72 h post infection and membranes prepared.

High five cells expressing $A_{2A}$ receptors were homogenized in 50 mM tris-buffer pH 7.4 in an ultra Turrax homogenisator. The membranes were diluted to a concentration of 0.6 mg/ml and 2 U Adenosine deaminase (Roche)/ml membrane suspension was added. The solution was preincubated 30 min at 37° C. before use.

$A_{2A}$ Binding Analysis:

Binding assay was performed in 96 well flat bottom plate and initiated by mixing 10.6 μg protein/well with solutions of standard compounds or test compounds (final concentrations 0-10 μM) and 1 nM final concentration of $^3$H-ZM241385 (R1036 from Tocris). All test compounds were diluted in 50 nM trisbuffer from DMSO-stocks (2 mM or 10 mM). The reactions (final volume=200 μL) were incubated for 30 min at 25° C. and washed on Unifilter-GF/B with water. The filters were dried 20 min (37° C.) before addition of 35 μl Microscient-0 or Optiphase supermix and counting in a Trilux counter for 1 min.

The data were fitted with non-linear regression, and $IC_{50}$ and $K_i$ values were calculated from the equations:

$$IC_{50}=([I]/(100/(100-\%\,INH))/(1+([L]/K_D)$$

and $$K_i=IC_{50}/(1-[L]/K_D),$$

where [I] is the inhibitor concentration, and [L] and $K_D$ are concentration and dissociation equilibrium constant of the radiotracer, respectively. The exemplified compounds I-93 of the invention are $A_{2A}$-receptor ligands, such as antagonists, agonists, reverse agonists or partial agonists having a human $A_{2A}$ binding affinity ($K_i$) of 210 nM or less.

Formulation Examples

The pharmaceutical formulations of the invention may be prepared by conventional methods in the art.

For example: Tablets may be prepared by mixing the active ingredient with ordinary adjuvants and/or diluents and subsequently compressing the mixture in a conventional tabletting machine. Examples of adjuvants or diluents comprise: Corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to the desired volume, sterilising the solution and filling it in suitable ampoules or vials. Any suitable additive conventionally used in the art may be added, such as tonicity agents, preservatives, antioxidants, etc.

Typical examples of recipes for the formulation of the invention are as follows:

2) Tablets containing 5.0 mg of a compound of the invention calculated as the free base:

| | |
|---|---|
| Compound 1 | 5.0 mg |
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |

2) Tablets containing 0.5 mg of a compound of the invention calculated as the free base:

| | |
|---|---|
| Compound 1 | 0.5 mg |
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |

3) Syrup containing per millilitre:

| | |
|---|---|
| Compound 1 | 25 mg |
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 mL |
| Flavour | 0.05 mg |
| Saccharin sodium | 0.5 mg |
| Water | ad 1 mL |

4) Solution for injection containing per millilitre:

| | |
|---|---|
| Compound 1 | 0.5 mg |
| Sorbitol | 5.1 mg |
| Acetic Acid | 0.05 mg |
| Saccharin sodium | 0.5 mg |
| Water | ad 1 mL |

The invention claimed is:

1. A compound of formula I

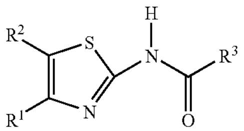

I wherein $R^1$ is phenyl optionally substituted with one or more substituents selected from halogen, $C_{1-6}$-alkyl and $C_{1-6}$-alkoxy;

$R^2$ is a five membered heteroaryl selected from the group consisting of [1,2,4]-oxadiazol-3-yl, [1,2,4]-oxadiazol-5-yl and [1,2,5]-oxadiazol-3-yl, wherein the heteroaryl is optionally substituted with one or more substituents selected from the group consisting of $C_{1-6}$-alkyl, phenyl-$C_{1-6}$-alkyl, $C_{1-6}$-alkoxy and $C_{1-6}$-alkoxy-$C_{1-6}$-alkyl, or $R^2$ is 5-oxo-4,5-dihydro-[1,3,4]-oxadiazol-2-yl;

and $R^3$ is selected from the group consisting of $C_{1-6}$-alkyl, $C_{3-8}$-cycloalkyl, $C_{3-8}$-cycloalkyl-$C_{1-6}$-alkyl, furanyl, furanyl-$C_{1-6}$-alkyl, thienyl, thienyl-$C_{1-6}$-alkyl, phenyl, phenyl -$C_{2-6}$-alkene and phenyl-$C_{1-6}$-alkyl, wherein the phenyl-$C_{1-6}$-alkyl optionally is substituted in the phenyl ring with one or more substituents selected from halogen, $C_{1-6}$-alkyl and $C_{1-6}$-alkoxy;

or a pharmaceutically acceptable addition salt thereof.

2. The compound according to claim 1, wherein $R^1$ is phenyl.

3. The compound according to claim 1, wherein $R^2$ is [1,2,4]-oxadiazol-3-yl optionally substituted with one or more substituents selected from the group consisting of $C_{1-6}$-alkyl, phenyl-$C_{1-6}$-alkyl, $C_{1-6}$-alkoxy and $C_{1-6}$-alkoxy-$C_{1-6}$-alkyl.

4. The compound according to claim 1, wherein $R^2$ is [1,2,4]-oxadiazol-5-yl optionally substituted with one or more substituents selected from the group consisting of $C_{1-6}$-alkyl, phenyl-$C_{1-6}$-alkyl, $C_{1-6}$-alkoxy and $C_{1-6}$-alkoxy-$C_{1-6}$-alkyl.

5. The compound according to claim 1, wherein $R^2$ is [1,2,5]-oxadiazol-3-yl optionally substituted with one or more substituents selected from the group consisting of $C_{1-6}$-alkyl, phenyl-$C_{1-6}$-alkyl, $C_{1-6}$-alkoxy and $C_{1-6}$-alkoxy-$C_{1-6}$-alkyl.

6. The compound according to claim 1, wherein $R^2$ is 5-oxo-4,5-dihydro-[1,3,4]-oxadiazol-2-yl.

7. The compound according to claim 1, wherein $R^3$ is selected from the group consisting of $C_{1-6}$-alkyl, $C_{3-8}$-cycloalkyl, $C_{3-8}$-cyclo-alkylmethyl, furan-2-yl, furan-3-yl, thien-2-yl, thien-2-yl-methyl, thien-3-yl, phenylmethyl, phenethylene and benzyl optionally substituted in the phenyl ring.

8. The compound according to claim 7, wherein the benzyl is substituted with one or two methoxy groups in the phenyl ring.

9. The compound according to claim 7, wherein the benzyl is substituted in the 3-position, 4-position or both the 3- and 4-positions of the phenyl ring.

10. The compound according to claim 1, selected from the group consisting of:

2-(3,4-dimethoxy-phenyl)-N-(5-[1,2,4]oxadiazol-3-yl-4-phenyl-thiazol-2-yl)-acetamide, cyclopropanecarboxylic acid (5-[1,2,4]oxadiazol-3-yl-4-phenyl-thiazol-2-yl)-amide, 2-cyclopentyl-N-(5-[1,2,4]oxadiazol-3-yl-4-phenyl-thiazol-2-yl)-acetamide, 2-(3-methoxy-phenyl)-N-(5-[1,2,4]oxadiazol-3-yl-4-phenyl-thiazol-2-yl)-acetamide, furan-2-carboxylic acid [5-(3-methyl-[1,2,4]oxadiazol-5-yl)-4-phenyl-thiazol-2-yl]-amide, 3,3-dimethyl-N-[5-(5-methyl-[1,2,4]oxadiazol-3-yl)-4-phenyl-thiazol-2-yl]-butyramide, N-[5-(3-methyl-[1,2,4]oxadiazol-5-yl)-4-phenyl-thiazol-2-yl]-benzamide, N-[5-(3-ethyl-[1,2,4]oxadiazol-5-yl)-4-phenyl-thiazol-2-yl]-benzamide, N-[5-(5-methyl-[1,2,4]oxadiazol-3-yl)-4-phenyl-thiazol-2-yl]-benzamide, cyclopropanecarboxylic acid [5-(3-methyl-[1,2,4]oxadiazol-5-yl)-4-phenyl-thiazol-2-yl]-amide, cyclopropanecarboxylic acid [5-(3-ethyl-[1,2,4]oxadiazol-5-yl)-4-phenyl-thiazol-2-yl]-amide, cyclopropanecarboxylic acid [5-(5-methyl-[1,2,4]oxadiazol-3-yl)-4-phenyl-thiazol-2-yl]-amide, cyclopropanecarboxylic acid [5-(5-ethyl-[1,2,4]oxadiazol-3-yl)-4-phenyl-thiazol-2-yl]-amide, 2-cyclopentyl-N-[5-(3-methyl-[1,2,4]oxadiazol-5-yl)-4-phenyl-thiazol-2-yl]-acetamide, 2-cyclopentyl-N-[5-(3-ethyl-[1,2,4]oxadiazol-5-yl)-4-phenyl-thiazol-2-yl]-acetamide, 2-cyclopentyl-N-[5-(5-methyl-[1,2,4]oxadiazol-3-yl)-4-phenyl-thiazol-2-yl]-acetamide, 2-cyclopentyl-N-[5-(5-ethyl-[1,2,4]oxadiazol-3-yl)-4-phenyl-thiazol-2-yl]-acetamide, cyclohexanecarboxylic acid [5-(3-methyl-[1,2,4]oxadiazol-5-yl)-4-phenyl-thiazol-2-yl]-amide, cyclohexanecarboxylic acid [5-(3-ethyl-[1,2,4]oxadiazol-5-yl)-4-phenyl-thiazol-2-yl]-amide, cyclohexanecarboxylic acid [5-(5-methyl-[1,2,4]oxadiazol-3-yl)-4-phenyl-thiazol-2-yl]-amide, N-[5-(3-ethyl-[1,2,4]oxadiazol-5-yl)-4-phenyl-thiazol-2-yl]-isobutyramide, 3-methyl-N-[5-(3-methyl-[1,2,4]oxadiazol-5-yl)-4-phenyl-thiazol-2-yl]-butyramide, N-[5-(3-ethyl-[1,2,4]oxadiazol-5-yl)-4-phenyl-thiazol-2-yl]-3-methyl-butyramide, 3-methyl-N-[5-(5-methyl-[1,2,4]oxadiazol-3-yl)-4-phenyl-thiazol-2-yl]-butyramide, N-[5-(3-methyl-[1,2,4]oxadiazol-5-yl)-4-phenyl-thiazol-2-yl]-propionamide, N-[5-(3-ethyl-[1,2,4]oxadiazol-5-yl)-4-phenyl-thiazol-2-yl]-propionamide, N-[5-(5-methyl-[1,2,4]oxadiazol-3-yl)-4-phenyl-thiazol-2-yl]-propionamide, N-[5-(3-methyl-[1,2,4]oxadiazol-5-yl)-4-phenyl-thiazol-2-yl]-2-phenyl-acetamide, N-[5-(3-ethyl-[1,2,4]oxadiazol-5-yl)-4-phenyl-thiazol-2-yl]-2-phenyl-acetamide, N-[5-(5-methyl-[1,2,4]oxadiazol-3-yl)-4-phenyl-thiazol-2-yl]-2-phenyl-acetamide, N-[5-(5-Oxo-4,5-dihydro-[1,3,4]oxadiazol-2-yl)-4-phenyl-thiazol-2-yl]-2-phenyl-acetamide, N-[5-(5-ethyl-[1,2,4]oxadiazol-3-yl)-4-phenyl-thiazol-2-yl]-3-phenyl-acrylamide, hexanoic acid [5-(3-methyl-[1,2,4]oxadiazol-5-yl)-4-phenyl-thiazol-2-yl]-amide, hexanoic acid [5-(5-methyl-[1,2,4]oxadiazol-3-yl)-4-phenyl-thiazol-2-yl]-amide, N-[5-(3-methyl-[1,2,4]oxadiazol-5-yl)-4-phenyl-thiazol-2-yl]-2-thiophen-2-yl-acetamide, N-[5-(3-ethyl-[1,2,4]oxadiazol-5-yl)-4-phenyl-thiazol-2-yl]-2-thiophen-2-yl-acetamide, N-[5-(5-methyl-[1,2,4]oxadiazol-3-yl)-4-phenyl-thiazol-2-yl]-2-thiophen-2-yl-acetamide, N-[5-(3-methyl-[1,2,4]oxadiazol-5-yl)-4-phenyl-thiazol-2-yl]-acetamide, N-[5-(3-ethyl-[1,2,4]oxadiazol-5-yl)-4-phenyl-thiazol-2-yl]-acetamide, N-[5-(5-methyl-[1,2,4]oxadiazol-3-yl)-4-phenyl-thiazol-2-yl]-acetamide, 2,2-dimethyl-N-[5-(3-methyl-[1,2,4]oxadiazol-5-yl)-4-phenyl-thiazol-2-yl]-propionamide, N-[5-(3-ethyl-[1,2,4]oxadiazol-5-yl)-4-phenyl-thiazol-2-yl]-2,2-dimethyl-propionamide, 2,2-dimethyl-N-[5-(5-methyl-[1,2,4]oxadiazol-3-yl)-4-phenyl-thiazol-2-yl]-propionamide, thiophene-3-carboxylic acid [5-(3-methyl-[1,2,4]oxadiazol-5-yl)-4-phenyl-thiazol-2-yl]-amide, and thiophene-3-carboxylic acid [5-(5-methyl-[1,2,4]oxadiazol-3-yl)-4-phenyl-thiazol-2-yl]-amide or a pharmaceutically acceptable addition salt thereof.

* * * * *